United States Patent
Yu et al.

(10) Patent No.: US 9,090,944 B2
(45) Date of Patent: Jul. 28, 2015

(54) BIOMARKER DACT1 FOR GASTRIC CANCER

(75) Inventors: Jun Yu, Lake Silver (HK); Joseph Jao Yiu Sung, Shatin (HK); Shiyan Wang, Shatin (HK)

(73) Assignee: The Chinese University of Hong Kong, Shatin, N.T. (HK)

( * ) Notice: Subject to any disclaimer, the term of this patent is extended or adjusted under 35 U.S.C. 154(b) by 36 days.

(21) Appl. No.: 13/328,785

(22) Filed: Dec. 16, 2011

(65) Prior Publication Data

US 2013/0157879 A1 Jun. 20, 2013

(51) Int. Cl.
*C12Q 1/68* (2006.01)
*G01N 33/574* (2006.01)

(52) U.S. Cl.
CPC ........ *C12Q 1/6886* (2013.01); *G01N 33/57446* (2013.01); *C12Q 2600/154* (2013.01); *C12Q 2600/158* (2013.01)

(58) Field of Classification Search
None
See application file for complete search history.

(56) References Cited

FOREIGN PATENT DOCUMENTS

| CN | 101909630 A | 12/2010 | |
| WO | 2007/149269 A2 | 12/2007 | |
| WO | WO2009108917 | * 3/2009 | ............. C12Q 12/68 |
| WO | 2009/058102 A1 | 8/2009 | |

OTHER PUBLICATIONS

Wang et al (Gastroenterology, May 2011. vol. 140, No. 5, Suppl.1, pp. S157. Meeting abstract).*
Otani et al. (Expert Review in Molecular Diagnostics, 2013, vol. 13, No. 5, pp. 445-455).*
Takai et al.; "The CpG island searcher: a new WWW resource"; *In Silico Biology*; vol. 3 (2003) 6 pages.
Tao et al.; "Defective de novo methylation of viral and cellular DNA sequences in ICF syndrome cells"; *Human Molecular Genetics*; 11(18):2091-2102 (2002).
Yau et al.; "HDPR1, a novel inhibitor of the WNT/beta-catenin signaling, is frequently downregulated in hepatocellular carcinoma: involvement of methylation-mediated gene silencing"; *Oncogene*; 24(9):1607-14. (Feb. 2005).
Zhang et al., "Dapper 1 Antagonizes Wnt Signaling by Promoting Dishevelled Degradation", *Journal of Biological Chemistry*, vol. 281, No. 13, pp. 8607-8612 (2006).
NCBI GenBank accession No. BK000256, Feb. 3, 2006.

* cited by examiner

*Primary Examiner* — Celine Qian
(74) *Attorney, Agent, or Firm* — Kilpatrick Townsend & Stockton LLP

(57) ABSTRACT

The present invention provides a method for diagnosing and determining prognosis of gastric cancer in a subject by detecting suppressed expression of the DACT1 gene, which in some cases is due to elevated methylation level in the genomic sequence of this gene. A kit and device useful for such a method are also provided. In addition, the present invention provides a method for treating gastric cancer by increasing DACT1 gene expression or activity.

10 Claims, 9 Drawing Sheets

A

B

US 9,090,944 B2

BIOMARKER DACT1 FOR GASTRIC CANCER

REFERENCE TO A "SEQUENCE LISTING," A TABLE, OR A COMPUTER PROGRAM LISTING APPENDIX SUBMITTED AS AN ASCII TEXT FILE

The Sequence Listing written in file -100.TXT, created on Jan. 25, 2012, 20,480 bytes, machine format IBM-PC, MS-Windows operating system, is hereby incorporated by reference in its entirety for all purposes.

BACKGROUND OF THE INVENTION

Gastric cancer, also known as stomach cancer, is the fourth most common cancer worldwide with approximately 1,000,000 cases diagnosed annually. It is a disease with a high mortality rate (about 800,000 deaths per year), making it the second most common cause of cancer death worldwide after lung cancer. The incidence of gastric cancer is significantly higher among men and in developing nations, including many Asian countries.

Gastric cancer often remains asymptomatic or exhibits only nonspecific symptoms in its early stages, diagnosis in many cases is therefore not made until the disease has reached an advanced stage. This leads to a generally poor prognosis: metastasis occurs in 80-90% of individuals diagnosed with gastric cancer, with a six-month survival rate of 65% in those diagnosed in early stages and less than 15% of those diagnosed in late stages.

Because of the prevalence of gastric cancer and its grave implications on patients' life expectancy, there exists a need for new methods to diagnose, monitor, and treat gastric cancer. This invention fulfills this and other related needs.

BRIEF SUMMARY OF THE INVENTION

In a first aspect, the present invention provides a method for detecting gastric cancer in a subject. The method includes the steps of: (a) measuring expression level of DACT1 in a sample taken from the subject, and (b) comparing the expression level obtained in step (a) with a standard control. When a decrease in the expression level of DACT1 is detected as compared with the standard control, it indicates that the subject may have gastric cancer. Typically, the sample used in the method is a stomach mucosa sample, e.g., one that includes stomach epithelial cells.

In some embodiments, the expression level of DACT1 is the DACT1 protein level. In other embodiments, the expression level of DACT1 is DACT1 mRNA level. When the DACT1 protein level is measured, step (a) may include an immunoassay using an antibody that specifically binds the DACT1 protein. For example, a Western Blot analysis may be used. In other cases, step (a) may involve mass spectrometry, or a hybridization-based assay such as hybridization to a microarray, fluorescence probe, or molecular beacon.

When DACT1 mRNA level is measured, step (a) in some cases may involve an amplification reaction, such as a polymerase chain reaction (PCR), especially a reverse transcriptase-PCR(RT-PCR). In other cases, the detecting step may involve a polynucleotide hybridization assay, such as a Southern Blot analysis or Northern Blot analysis or an in situ hybridization assay. For example, a polynucleotide probe may be used in the polynucleotide hybridization assay to hybridize with SEQ ID NO:1, 4, or 6 or a complement thereof. In some cases, the polynucleotide probe may include a detectable moiety.

In some embodiments, when the subject is indicated as having gastric cancer after the first round of method steps described above, the claimed method may further include repeating step (a) at a later time using the sample type of sample from the subject. An increase in the expression level of DACT1 at the later time as compared to the amount from the original step (a) indicates an improvement of gastric cancer, whereas a decrease indicates a worsening of gastric cancer.

In a second aspect, the present invention provides a method for detecting gastric cancer in a subject. The method includes the steps of: (a) treating a sample taken from the subject with an agent that differentially modifies methylated and unmethylated DNA; and (b) determining whether each CpG in a CpG-containing genomic sequence is methylated or unmethylated, with the CpG-containing genomic sequence being at least a segment of SEQ ID NO:1 or 6 and comprising at least one CpG. When the presence of one methylated CpG is detected in the CpG-containing genomic sequence, it indicates that the subject may have gastric cancer.

In some embodiments, the CpG-containing genomic sequence contains two or more CpG, and when at least 50% of all CpG being methylated the subject is indicated as having gastric cancer. In some cases, the CpG-containing genomic sequence is a segment of at least 15, 20, 50, or more contiguous nucleotides of SEQ ID NO:1 or 6. In other cases, the CpG-containing genomic sequence is SEQ ID NO:1 or 6. In one embodiment of the claimed method, the CpG-containing genomic sequence is SEQ ID NO:6, and when at least 5 of all CpG in the CpG-containing genomic sequence are methylated, the subject is indicated as likely having gastric cancer.

In some examples, the sample used in the claimed method is a stomach mucosa sample. In other examples, when the subject is indicated as having gastric cancer after the first round of method steps described above, the method further involves repeating steps (a) and (b) at a later time using the sample type of sample from the subject. When an increase is detected in the number of methylated CpG at the later time as compared to the number of methylated CpG determined from the original step (b), it indicates a worsening of gastric cancer, whereas a decrease indicates an improvement of gastric cancer.

In some embodiments, the agent used in the claimed method to differentially modify methylated DNA and unmethylated DNA is an enzyme that preferentially cleaves methylated DNA, an enzyme that preferentially cleaves unmethylated DNA, or a bisulfite. In other embodiments, step (b) of the method involves an amplification reaction; or step (b) may involve sequencing of a DNA molecule.

In a third aspect, the present invention provides a kit for detecting gastric cancer in a subject, comprising (1) a standard control that provides an average amount of DACT1 protein or DACT1 mRNA; and (2) an agent that specifically and quantitatively identifies DACT1 protein or DACT1 mRNA. In some cases, the agent may be an antibody that specifically binds the DACT1 protein; or the agent may be a polynucleotide probe that hybridizes with the DACT1 mRNA. For example, the polynucleotide probe has the nucleotide sequence set forth in SEQ ID NO:1, 4, or 6 or a complement thereof. The agent may include a detectable moiety. In other cases, the kit may further comprise two oligonucleotide primers for specifically amplifying at least a segment of SEQ ID NO:2 or 3 or its complement in an amplification reaction. Typically, the kit will further include an instruction manual.

In a fourth aspect, the present invention provides a method for inhibiting growth of a gastric cancer cell. The claimed method includes the step of contacting the gastric cancer cell with (1) an effective amount of a polypeptide that comprises the amino acid sequence set forth in SEQ ID NO:5 or (2) a nucleic acid that comprises a polynucleotide sequence encoding SEQ ID NO:5. In some embodiments, the nucleic acid is an expression cassette comprising a promoter operably linked to the polynucleotide sequence encoding SEQ ID NO:5. Various promoters may be useful in this method, for example, the promoter may be an epithelium-specific promoter. In other embodiments, the nucleic acid comprises the polynucleotide sequence set forth in SEQ ID NO:2 or 3. In yet other embodiments, the gastric cancer cell is within a patient's body.

In a fifth aspect, the present invention provides an isolated nucleic acid having the nucleotide sequence at least 95% identical to a segment of about 20-100 contiguous nucleotides of SEQ ID NO:1, 2, 3, 4, or 6 or complement thereof. In some embodiments, the nucleic acid has the nucleotide sequence identical to a segment of about 20-100 contiguous nucleotides of SEQ ID NO:1, 2, 3, 4, or 6 or complement thereof. In other embodiments, the nucleic acid is conjugated to a detectable moiety.

In addition, the present invention provides a kit for detecting gastric cancer. The kit comprises: (1) an agent that differentially modifies methylated and unmethylated DNA, and (2) an indicator that, after the agent has been used to treat a sample from a subject who is being tested for gastric cancer, determines whether each CpG in a CpG-containing genomic sequence is methylated or unmethylated. The CpG-containing genomic sequence is at least a segment of SEQ ID NO:1 or 6 and comprises at least one CpG. The present invention also provides a composition for inhibiting growth of a gastric cancer cell. The composition contains an effective amount of (1) a polypeptide comprising the amino acid sequence set forth in SEQ ID NO:5 (e.g., a polypeptide consisting of the amino acid sequence of SEQ ID NO:5) or (2) a nucleic acid comprising or consisting of a polynucleotide sequence encoding SEQ ID NO:5 (e.g., a nucleic acid sequence comprising the polynucleotide sequence of SEQ ID NO:2 or 3), and a pharmaceutically acceptable carrier. In this regard, this invention further provides the use of a polypeptide comprising the amino acid sequence set forth in SEQ ID NO:5 (e.g., a polypeptide consisting of the amino acid sequence of SEQ ID NO:5) or a nucleic acid comprising a polynucleotide sequence encoding SEQ ID NO:2 or 3 (e.g., a nucleic acid sequence comprising or consisting of the polynucleotide sequence of SEQ ID NO:2 or 3) in preparing a medicament for inhibiting growth of a gastric cancer cell. Moreover, the present invention provides a use of a polynucleotide sequence that comprises or consists of a segment of SEQ ID NO:1, 2, 3, 4, or 6 or complement thereof in preparing a kit for detecting gastric cancer. The segment is typically about 20-100 contiguous nucleotides of SEQ ID NO:1, 2, 3, 4, or 6, or its complement.

DEFINITIONS

Figure 1:
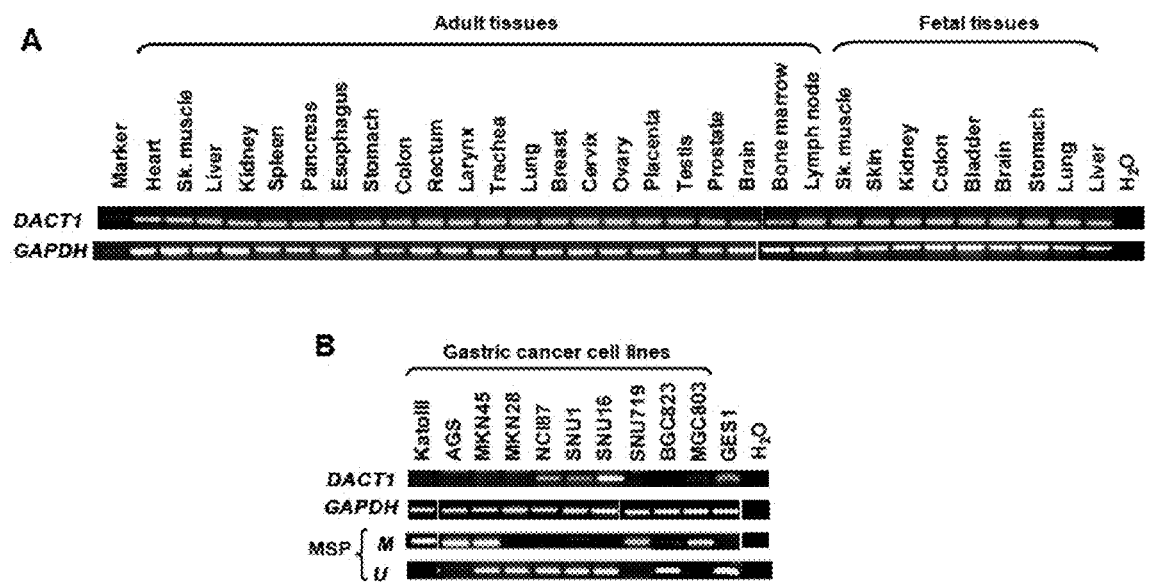
FIG. 1 shows DACT1 mRNA expression in normal tissues and gastric cell lines in an embodiment.

The term "DACT1 gene" or "DACT1 protein," as used herein, refers to any naturally occurring variants or mutants, interspecies homologs or orthologs, or man-made variants of human DACT1 gene or DACT1 protein. The human DACT1 gene is located on chromosome 14q23.1. The cDNA sequence of a human wild-type DACT1 gene is set forth in GenBank Accession No. NM_016651 (provided herein as SEQ ID NO:3), encoding a 798-amino acid DACT1 protein (provided herein as SEQ ID NO:5). A DACT1 protein within the meaning of this application typically has at least 80%, or 90%, or 95% or higher sequence identity to the human wild-type DACT1 protein.

In this disclosure the terms "gastric cancer" and "stomach cancer" have the same meaning and refer to a cancer of the stomach or of stomach cells. Such cancers may be adenocarcinomas that occur in the lining of the stomach (mucosa or stomach epithelium) and may be in pylorus, body, or cardial (lower, body and upper) parts of the stomach. A "gastric cancer cell" is a stomach epithelial cell possessing characteristics of gastric cancer and encompasses a precancerous cell, which is in the early stages of conversion to a cancer cell or which is predisposed for conversion to a cancer cell. Such cells may exhibit one or more phenotypic traits characteristic of the cancerous cells.

In this disclosure the term "or" is generally employed in its sense including "and/or" unless the content clearly dictates otherwise.

As used herein, the term "gene expression" is used to refer to the transcription of a DNA to form an RNA molecule encoding a particular protein (e.g., human DACT1 protein) or the translation of a protein encoded by a polynucleotide sequence. In other words, both mRNA level and protein level encoded by a gene of interest (e.g., human DACT1 gene) are encompassed by the term "gene expression level" in this disclosure.

In this disclosure the term "biological sample" or "sample" includes sections of tissues such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, stomach biopsy tissue etc. A biological sample is typically obtained from a eukaryotic organism, which may be a mammal, may be a primate and may be a human subject.

In this disclosure the term "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cell, stomach tissue, etc.) among other factors. Representative biopsy techniques include, but are not limited to, excisional biopsy, incisional biopsy, needle biopsy, surgical biopsy, and bone marrow biopsy and may comprise colonoscopy. A wide range of biopsy techniques are well known to those skilled in the art who will choose between them and implement them with minimal experimentation.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a variant DACT1 protein used in the method of this invention (e.g., for treating gastric cancer) has at least 80% sequence identity, preferably 85%, 90%, 91%, 92%, 93, 94%, 95%, 96%, 97%, 98%, 99%, or 100% identity, to a reference sequence, e.g., a wild-type human DACT1 protein), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Examples of algorithms that are suitable for determining percent sequence identity and sequence similarity are the BLAST and BLAST 2.0 algorithms, which are described in Altschul et al., (1990) J. Mol. Biol. 215: 403-410 and Altschul et al. (1977) Nucleic Acids Res. 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff and Henikoff, Proc. Natl. Acad. Sci. USA 89:10915 (1989)).

The BLAST algorithm also performs a statistical analysis of the similarity between two sequences (see, e.g., Karlin and Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that reacts differentially with methylated and unmethylated DNA in a process through which distinguishable products or quantitatively distinguishable results (e.g. degree of binding or precipitation) are generated from methylated and non-methylated DNA, thereby allowing the identification of the DNA methylation status. Such processes may include, but are not limited to, chemical reactions (such as an unmethylated C→U conversion by bisulfite), enzymatic treatment (such as cleavage by a methylation-dependent endonuclease), binding, and precipitation. Thus, an enzyme that preferentially cleaves methylated DNA is one capable of cleaving a DNA molecule at a much higher efficiency when the DNA is methylated, whereas an enzyme that preferentially cleaves unmethylated DNA exhibits a significantly higher efficiency when the DNA is not methylated. In the context of the present invention, a reagent that "differentially modifies" methylated and unmethylated DNA also refers to any reagent that exhibits differential ability in its binding to DNA sequences or precipitation of DNA sequences depending on their methylation status. One class of such reagents consists of methylated DNA binding proteins.

A "CpG-containing genomic sequence" as used herein refers to a segment of DNA sequence at a defined location in the genome of an individual. Typically, a "CpG-containing genomic sequence" is at least 15 contiguous nucleotides in length and contains at least one CpG pair. In some cases, it can be at least 18, 20, 25, 30, 50, 80, 100, 150, 200, 250, or 300 contiguous nucleotides in length and contains at least 2, 3, 4, 5, 6, 7, 8, 9, 10, 15, 20, 25, or 30 CpG pairs. For any one "CpG-containing genomic sequence" at a given location, e.g., within a region of the human DACT1 genomic sequence (such as the region containing the promoter and exon 1), nucleotide sequence variations may exist from individual to individual and from allele to allele even for the same individual. Furthermore, a "CpG-containing genomic sequence" may encompass a nucleotide sequence transcribed or not transcribed for protein production, and the nucleotide sequence can be a protein-coding sequence, a non protein-coding sequence (such as a transcription promoter), or a combination thereof.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce F(ab)'$_2$, a dimer of Fab which itself is a light chain joined to $V_H$-$C_H$1 by a disulfide bond. The F(ab)'$_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

As used in this application, an "increase" or a "decrease" refers to a detectable positive or negative change in quantity from a comparison control, e.g., an established standard control (such as an average expression level of DACT1 mRNA or protein found in non-cancerous stomach tissue). An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the cDNA or genomic sequence for human DACT1 or a portion thereof. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in Table 1 of the disclosure where their specific applications are indicated. In this disclosure the term "primer pair" means a pair of primers that hybridize to opposite strands a target DNA molecule or to regions of the target DNA which flank a nucleotide sequence to be amplified. In this disclosure the term "primer site", means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

"Standard control" as used herein refers to a predetermined amount or concentration of a polynucleotide sequence or polypeptide, e.g., DACT1 mRNA or protein, that is present in an established normal disease-free tissue sample, e.g., a normal stomach epithelial tissue sample. The standard control value is suitable for the use of a method of the present invention, to serve as a basis for comparing the amount of DACT1 mRNA or protein that is present in a test sample. An established sample serving as a standard control provides an average amount of DACT1 mRNA or protein that is typical for a stomach epithelial tissue sample (e.g., stomach mucosa) of an average, healthy human without any stomach disease especially gastric cancer as conventionally defined. A standard control value may vary depending on the nature of the sample as well as other factors such as the gender, age, ethnicity of the subjects based on whom such a control value is established.

The term "average," as used in the context of describing a human who is healthy, free of any stomach disease (especially gastric cancer) as conventionally defined, refers to certain characteristics, especially the amount of human DACT1 mRNA or DACT1 protein, found in the person's stomach tissue, e.g., epithelial tissue or gastric mucosa, that are representative of a randomly selected group of healthy humans who are free of any stomach diseases (especially gastric cancer). This selected group should comprise a sufficient number of humans such that the average amount of DACT1 mRNA or protein in the stomach mucosa among these individuals reflects, with reasonable accuracy, the corresponding amount of DACT1 mRNA/protein in the general population of healthy humans. In addition, the selected group of humans generally have a similar age to that of a subject whose stomach tissue sample is tested for indication of gastric cancer. Moreover, other factors such as gender, ethnicity, medical history are also considered and preferably closely matching between the profiles of the test subject and the selected group of individuals establishing the "average" value.

The term "amount" as used in this application refers to the quantity of a polynucleotide of interest or a polypeptide of interest, e.g., human DACT1 mRNA or protein, present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of an polynucleotide encoding DACT1 mRNA is the amount of said polynucleotide to achieve an increased level of DACT1 protein expression or biological activity, such that the symptoms of gastric cancer are reduced, reversed, eliminated, prevented, or delayed of the onset in a patient who has been given the polynucleotide for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, gastric cancer. Subjects also include individuals currently undergoing therapy that seek manipulation of the therapeutic regimen. Subjects or individuals in need of treatment include those that demonstrate symptoms of gastric cancer or are at risk of suffering from gastric cancer or its symptoms. For example, a subject in need of treatment includes individuals with a genetic predisposition or family history for gastric cancer, those that have suffered relevant symptoms in the past, those that have been exposed to a triggering substance or event, as well as those suffering from chronic or acute symptoms of the condition. A "subject in need of treatment" may be at any age of life.

"Inhibitors," "activators," and "modulators" of DACT1 protein are used to refer to inhibitory, activating, or modulating molecules, respectively, identified using in vitro and in vivo assays for DACT1 protein binding or signaling, e.g., ligands, agonists, antagonists, and their homologs and mimetics. The term "modulator" includes inhibitors and activators Inhibitors are agents that, e.g., partially or totally block carbohydrate binding, decrease, prevent, delay activation, inactivate, desensitize, or down regulate the activity of DACT1 protein. In some cases, the inhibitor directly or indirectly binds to DACT1 protein, such as a neutralizing antibody. Inhibitors, as used herein, are synonymous with inactivators and antagonists. Activators are agents that, e.g., stimulate, increase, facilitate, enhance activation, sensitize or up regulate the activity of DACT1 protein. Modulators include DACT1 protein ligands or binding partners, including modifications of naturally-occurring ligands and synthetically-designed ligands, antibodies and antibody fragments, antagonists, agonists, small molecules including carbohydrate-containing molecules, siRNAs, RNA aptamers, and the like.

DETAILED DESCRIPTION OF THE INVENTION

I. Introduction

Gastric cancer patients often face a grim prognosis due to the nature of this disease in its lacking of specific symptoms during its early development stages. Early detection of gastric cancer is therefore critical for improving patient survival rate.

The present inventors discovered for the first time that expression of DACT1 protein is suppressed in gastric cancer cells. This suppressed expression of DACT1 protein is due to increased methylation in the DACT1 genomic sequence, especially in the promoter region of the gene, which leads to decreased transcription of DACT1 mRNA. This discovery provides important means for detecting, monitoring, and treating gastric cancer.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of the human DACT1 gene, and synthetic oligonucleotides (e.g., primers) can be verified using, e.g., the chain termination method for sequencing double-stranded templates of Wallace et al., *Gene* 16: 21-26 (1981).

III. Acquisition of Tissue Samples and Analysis of DACT1 mRNA or DNA

The present invention relates to measuring the amount of DACT1 mRNA or analyzing the methylation pattern of DACT1 genomic DNA found in a person's stomach tissue, especially stomach epithelial sample, as a means to detect the presence, to assess the risk of developing, and/or to monitor the progression or treatment efficacy of gastric cancer. Thus, the first steps of practicing this invention are to obtain a stomach epithelial tissue sample from a test subject and extract mRNA or DNA from the sample.

A. Acquisition and Preparation of Stomach Tissue Samples

A stomach tissue sample is obtained from a person to be tested or monitored for gastric cancer using a method of the present invention. Collection of stomach epithelial tissue sample from an individual is performed in accordance with the standard protocol hospitals or clinics generally follow, such as during an endoscopy. An appropriate amount of stomach epithelium is collected and may be stored according to standard procedures prior to further preparation.

The analysis of DACT1 mRNA or DNA found in a patient's stomach epithelial sample according to the present invention may be performed using, e.g., stomach mucosa. The methods for preparing tissue samples for nucleic acid extraction are well known among those of skill in the art. For example, a subject's stomach mucosa sample should be first treated to disrupt cellular membrane so as to release nucleic acids contained within the cells.

B. Extraction and Quantitation of RNA

There are numerous methods for extracting mRNA from a biological sample. The general methods of mRNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract®Series 9600™ (Promega, Madison, Wis.), may also be used to obtain mRNA from a biological sample from a test subject. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

1. PCR-Based Quantitative Determination of mRNA Level

Once mRNA is extracted from a sample, the amount of human DACT1 mRNA may be quantified. The preferred method for determining the mRNA level is an amplification-based method, e.g., by polymerase chain reaction (PCR), especially reverse transcription-polymerase chain reaction (RT-PCR).

Prior to the amplification step, a DNA copy (cDNA) of the human DACT1 mRNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target mRNA is typically used in practicing the present invention. One of skill in the art will recognize, however, that amplification of these mRNA species in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA markers in maternal blood. For a review of branched-DNA signal amplification for direct quantitation of nucleic acid sequences in clinical samples, see Nolte, *Adv. Clin. Chem.* 33:201-235, 1998.

2. Other Quantitative Methods

The DACT1 mRNA can also be detected using other standard techniques, well known to those of skill in the art. Although the detection step is typically preceded by an amplification step, amplification is not required in the methods of the invention. For instance, the mRNA may be identified by size fractionation (e.g., gel electrophoresis), whether or not proceeded by an amplification step. After running a sample in an agarose or polyacrylamide gel and labeling with ethidium bromide according to well known techniques (see, e.g., Sambrook and Russell, supra), the presence of a band of the same size as the standard comparison is an indication of the presence of a target mRNA, the amount of which may then be compared to the control based on the intensity of the band. Alternatively, oligonucleotide probes specific to DACT1 mRNA can be used to detect the presence of such mRNA species and indicate the amount of mRNA in comparison to the standard comparison, based on the intensity of signal imparted by the probe.

Sequence-specific probe hybridization is a well known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, In situ Hybridization, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well known techniques. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^3H$, $^{125}I$, $^{35}S$, $^{14}C$, or $^{32}P$, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255:137-149, 1983.

C. Detection of Methylation in DACT1 Genomic Sequence

Methylation status of a segment of DACT1 genomic sequence containing one or more CpG (cytosine-guanine dinucleotide) pairs is investigated to provide indication as to whether a test subject is suffering from gastric cancer, whether the subject is at risk of developing gastric cancer, or whether the subject's gastric cancer is worsening or improving.

Typically a segment of the DACT1 genomic sequence that includes the 5' untranslated region (such as the promoter region) and includes one or more CpG nucleotide pairs is analyzed for methylation pattern. For example, SEQ ID NO:1 or 6 or a portion thereof can be used to determine how many of the CpG pairs within the sequence are methylated and how many are not methylated. The sequence being analyzed should be long enough to contain at least 1 CpG dinucleotide pair and detection of methylation at this CpG site is typically adequate indication of the presence of gastric cancer cells. The length of the sequence being analyzed is usually at least 15 or 20 contiguous nucleotides, and may be longer with at least 25, 30, 50, 100, 200, 300, 400, or more contiguous nucleotides. At least one, typically 2 or more, often 3, 4, 5, 6, 7, 8, 9, or more, CpG nucleotide pairs are present within the sequence. In the cases of multiple (2 or more) CpG sites are analyzed for methylation status, when at least 50% of the CpG pairs within the analyzed genomic sequence are shown to be methylated, subject being tested is deemed to have gastric cancer or have an elevated risk of developing gastric cancer. As an example, SEQ ID NO:1, a segment of DACT1 genomic sequence (−566 to −383 in relation to the transcription start site), and SEQ ID NO:6, a segment of DACT1 genomic sequence (−18 to+1102 in relation to the transcription start site), contain several CpG pairs. Some or majority of the CpG pairs in this region are found to be methylated in established gastric cancer cell lines and samples taken from gastric cancer, whereas non-cancerous stomach epithelial cells showed very few, if any at all, methylated CpG sites, For the purpose of determining the methylation pattern of a DACT1 genomic sequence, bisulfite treatment followed by DNA sequencing is particularly useful, since bisulfite converts an unmethylated cytosine (C) to a uracil (U) while leaving methylated cytosines unchanged, allowing immediate identification through a DNA sequencing process. Optionally, an amplification process such as PCR is included after the bisulfite conversion and before the DNA sequencing.

1. DNA Extraction and Treatment

Methods for extracting DNA from a biological sample are well known and routinely practiced in the art of molecular biology, see, e.g., Sambrook and Russell, supra. RNA contamination should be eliminated to avoid interference with DNA analysis. The DNA is then treated with a reagent capable of modifying DNA in a methylation differential manner, i.e., different and distinguishable chemical structures will result from a methylated cytosine (C) residue and an unmethylated C residue following the treatment. Typically, such a reagent reacts with the unmethylated C residue(s) in a DNA molecule and converts each unmethylated C residue to a uracil (U) residue, whereas the methylated C residues remain unchanged. This unmethylated C→U conversion allows detection and comparison of methylation status based on changes in the primary sequence of the nucleic acid. An exemplary reagent suitable for this purpose is bisulfite, such as sodium bisulfite. Methods for using bisulfite for chemical modification of DNA are well known in the art (see, e.g., Herman et al., *Proc. Natl. Acad. Sci. USA* 93:9821-9826, 1996).

As a skilled artisan will recognize, any other reagents that are unnamed here but have the same property of chemically (or through any other mechanism) modifying methylated and unmethylated DNA differentially can be used for practicing the present invention. For instance, methylation-specific modification of DNA may also be accomplished by methylation-sensitive restriction enzymes, some of which typically cleave an unmethylated DNA fragment but not a methylated DNA fragment, while others (e.g., methylation-dependent endonuclease McrBC) cleave DNA containing methylated cytosines but not unmethylated DNA. In addition, a combination of chemical modification and restriction enzyme treatment, e.g., combined bisulfite restriction analysis (COBRA) (Xiong et al. 1997 *Nucleic Acids Res.* 25(12): 2532-2534), is useful for practicing the present invention. Other available methods for detecting DNA methylation include, for example, methylation-sensitive restriction endonucleases (MSREs) assay by either Southern blot or PCR analysis, methylation specific or methylation sensitive-PCR (MS-PCR), methylation-sensitive single nucleotide primer extension (Ms-SnuPE), high resolution melting (HRM) analysis, bisulifte sequencing, pyrosequencing, methylation-specific single-strand conformation analysis (MS-SSCA), methylation-specific denaturing gradient gel electrophoresis (MS-DGGE), methylation-specific melting curve analysis (MS-MCA), methylation-specific denaturing high-performance liquid chromatography (MS-DHPLC), methylation-specific microarray (MSO). These assays can be either PCR analysis, quantitative analysis with fluorescence labelling or Southern blot analysis. Exemplary methylation sensitive DNA cleaving reagent such as restriction enzymes include AatII, AciI, AclI, AgeI, AscI, Asp718, AvaI, BbrPI, BceAI, BmgBI, BsaAI, BsaHI, BsiEI, BsiWI, BsmBI, BspDI, BsrFI, BssHII, BstBI, BstUI, ClaI, EagI, EagI-HF™, FauI, FseI, FspI, HaeII, HgaI, HhaI, HinP1I, HpaII, Hpy991, HpyCH41V, KasI, MluI, NarI, NgoMIV, NotI, NotI-HF™, NruI, Nt.BsmAI, PaeR71, PspXI, PvuI, RsrII, SacII, SalI, SalI-HF™, SfoI, SgrAI, SmaI, SnaBI or TspMI.

2. Optional Amplification and Sequence Analysis

Following the modification of DNA in a methylation-differential manner, the treated DNA is then subjected to sequence-based analysis, such that the methylation status of the DACT1 genomic sequence may be determined. An amplification reaction is optional prior to the sequence analysis after methylation specific modification. A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

Although PCR amplification is typically used in practicing the present invention, one of skill in the art will recognize that amplification of the relevant genomic sequence may be accomplished by any known method, such as the ligase chain reaction (LCR), transcription-mediated amplification, and self-sustained sequence replication or nucleic acid sequence-based amplification (NASBA), each of which provides sufficient amplification.

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes (e.g., C→U) in a polynucleotide sequence for practicing the methods of the present invention include but are not limited to mass spectrometry, primer extension, polynucleotide hybridization, real-time PCR, melting curve analysis, high resolution melting analysis, heteroduplex analysis, pyrosequencing, and electrophoresis.

IV. Quantitation of Polypeptides

A. Obtaining Samples

The first step of practicing the present invention is to obtain a sample of stomach epithelium from a subject being tested, assessed, or monitored for gastric cancer, the risk of developing gastric cancer, or the severity/progression of the condition. Samples of the same type should be taken from both a control group (normal individuals not suffering from any stomach disorder especially neoplasia) and a test group (subjects being tested for possible gastric cancer, for example). Standard procedures routinely employed in hospitals or clinics are typically followed for this purpose, as stated in the previous section.

For the purpose of detecting the presence of gastric cancer or assessing the risk of developing gastric cancer in test subjects, individual patients' stomach mucosa samples may be taken and the level of human DACT1 protein may be measured and then compared to a standard control. If a decrease in the level of human DACT1 protein is observed when compared to the control level, the test subject is deemed to have gastric cancer or have an elevated risk of developing the condition. For the purpose of monitoring disease progression or assessing therapeutic effectiveness in gastric cancer patients, individual patient's stomach epithelial samples may be taken at different time points, such that the level of human DACT1 protein can be measured to provide information indicating the state of disease. For instance, when a patient's DACT1 protein level shows a general trend of increase over time, the patient is deemed to be improving in the severity of gastric cancer or the therapy the patient has been receiving is deemed effective. A lack of change in a patient's DACT1 protein level or a continuing trend of decrease on other hand would indicate a worsening of the condition and ineffectiveness of the therapy given to the patient. Generally, a lower DACT1 protein level seen in a patient indicates a more severe form of the gastric cancer the patient is suffering from and a worse prognosis of the disease, as manifested in shorter life expectancy, higher rate of metastasis, resistance to therapy etc.

B. Preparing Samples for DACT1 Protein Detection

The stomach tissue sample from a subject is suitable for the present invention and can be obtained by well known methods and as described in the previous section. In certain applications of this invention, stomach mucosa may be the preferred sample type.

C. Determining the Level of Human DACT1 Protein

A protein of any particular identity, such as DACT1 protein, can be detected using a variety of immunological assays. In some embodiments, a sandwich assay can be performed by capturing the polypeptide from a test sample with an antibody having specific binding affinity for the polypeptide. The polypeptide then can be detected with a labeled antibody having specific binding affinity for it. Such immunological assays can be carried out using microfluidic devices such as microarray protein chips. A protein of interest (e.g., human DACT1 protein) can also be detected by gel electrophoresis (such as 2-dimensional gel electrophoresis) and western blot analysis using specific antibodies. Alternatively, standard immunohistochemical techniques can be used to detect a given protein (e.g., human DACT1 protein), using the appropriate antibodies. Both monoclonal and polyclonal antibodies (including antibody fragment with desired binding specificity) can be used for specific detection of the polypeptide. Such antibodies and their binding fragments with specific binding affinity to a particular protein (e.g., human DACT1 protein) can be generated by known techniques.

Other methods may also be employed for measuring the level of DACT1 protein in practicing the present invention. For instance, a variety of methods have been developed based on the mass spectrometry technology to rapidly and accurately quantify target proteins even in a large number of samples. These methods involve highly sophisticated equipment such as the triple quadrupole (triple Q) instrument using the multiple reaction monitoring (MRM) technique, matrix assisted laser desorption/ionization time-of-flight tandem mass spectrometer (MALDI TOF/TOF), an ion trap instrument using selective ion monitoring SIM) mode, and the electrospray ionization (ESI) based QTOP mass spectrometer. See, e.g., Pan et al., *J Proteome Res.* 2009 February; 8(2):787-797.

V. Establishing a Standard Control

In order to establish a standard control for practicing the method of this invention, a group of healthy persons free of any stomach disease (especially any form of tumor such as gastric cancer) as conventionally defined is first selected. These individuals are within the appropriate parameters, if applicable, for the purpose of screening for and/or monitoring gastric cancer using the methods of the present invention. Optionally, the individuals are of same gender, similar age, or similar ethnic background.

The healthy status of the selected individuals is confirmed by well established, routinely employed methods including but not limited to general physical examination of the individuals and general review of their medical history.

Furthermore, the selected group of healthy individuals must be of a reasonable size, such that the average amount/concentration of human DACT1 mRNA or DACT1 protein in the stomach tissue sample obtained from the group can be reasonably regarded as representative of the normal or average level among the general population of healthy people. Preferably, the selected group comprises at least 10 human subjects.

Once an average value for the DACT1 mRNA or DACT1 protein is established based on the individual values found in each subject of the selected healthy control group, this average or median or representative value or profile is considered a standard control. A standard deviation is also determined during the same process. In some cases, separate standard controls may be established for separately defined groups having distinct characteristics such as age, gender, or ethnic background.

VI. Treatment of Gastric Cancer

By illustrating the correlation of suppressed expression of DACT1 protein and gastric cancer, the present invention further provides a means for treating patients suffering from gastric cancer: by way of increasing DACT1 protein expression or biological activity. As used herein, treatment of gastric cancer encompasses reducing, reversing, lessening, or eliminating one or more of the symptoms of gastric cancer, as well as preventing or delaying the onset of one or more of the relevant symptoms.

A. Increasing DACT1 Expression or Activity

1. Nucleic Acids Encoding DACT1 Proteins

Enhancement of DACT1 gene expression can be achieved through the use of nucleic acids encoding a functional DACT1 protein. Such nucleic acids can be single-stranded nucleic acids (such as mRNA) or double-stranded nucleic acids (such as DNA) that can translate into an active form of DACT1 protein under favorable conditions.

In one embodiment, the DACT1-encoding nucleic acid is provided in the form of an expression cassette, typically recombinantly produced, having a promoter operably linked to the polynucleotide sequence encoding the DACT1 protein. In some cases, the promoter is a universal promoter that directs gene expression in all or most tissue types; in other cases, the promoter is one that directs gene expression specifically in epithelial cells, especially in stomach epithelium. Administration of such nucleic acids can increase the DACT1 protein expression in the target tissue, e.g., stomach epithelium. Since the human DACT1 gene cDNA sequence is known as Genbank Accession No.: NM 016651 and provided herein as SEQ ID NO:3, one can derive a suitable DACT1-encoding nucleic acid from the sequence, species homologs, and variants of these sequences.

2. DACT1 Proteins

By directly administering an effective amount of an active DACT1 protein to a patient suffering from gastric cancer and exhibiting suppressed DACT1 protein expression or activity, the disease may also be effectively treated. For example, this can be achieved by administering a recombinantly produced DACT1 protein possessing its biological activity to the patient suffering from gastric cancer. Formulations and methods for delivering a protein- or polypeptide-based therapeutic agent are well known in the art.

3. Activators of DACT1 Protein

Increased DACT1 protein activity can be achieved with an agent that is capable of activating the expression of DACT1 protein or enhancing the activity of DACT1 protein. For example, a demethylating agent (e.g., 5-Aza) may be able to activate DACT1 gene expression by removing the suppression of DACT1 gene expression caused by methylation of the promoter region of this gene. Other activating agents may include transcriptional activators specific for the DACT1 promoter and/or enhancer. Such activating agents can be screened for and identified using the DACT1 expression assays described in the examples herein.

Agonists of the DACT1 protein, such as an activating antibody, are another kind of activators of the DACT1 protein. Such activators act by enhancing the biological activity of the DACT1 protein, typically (but not necessarily) by direct binding with the DACT1 protein and/or its interacting proteins. Preliminary screening for such agonists may start with a binding assay for identifying molecules that physically interact with DACT1 protein.

B. Pharmaceutical Compositions

1. Formulations

Compounds of the present invention are useful in the manufacture of a pharmaceutical composition or a medicament. A pharmaceutical composition or medicament can be administered to a subject for the treatment of gastric cancer.

Compounds used in the present invention, e.g., a DACT1 protein, a nucleic acid encoding DACT1 protein, or an activator of DACT1 gene expression, are useful in the manufacture of a pharmaceutical composition or a medicament comprising an effective amount thereof in conjunction or mixture with excipients or carriers suitable for application.

An exemplary pharmaceutical composition for enhancing DACT1 expression comprises (i) an express cassette comprising a polynucleotide sequence encoding a human DACT1 protein as described herein, and (ii) a pharmaceutically acceptable excipient or carrier.

The terms pharmaceutically-acceptable and physiologically-acceptable are used synonymously herein. The expression cassette may be provided in a therapeutically effective dose for use in a method for treatment as described herein.

A DACT1 protein or a nucleic acid encoding a DACT1 protein can be administered via liposomes, which serve to target the conjugates to a particular tissue, as well as increase the half-life of the composition. Liposomes include emulsions, foams, micelles, insoluble monolayers, liquid crystals, phospholipid dispersions, lamellar layers and the like. In these preparations the inhibitor to be delivered is incorporated as part of a liposome, alone or in conjunction with a molecule which binds to, e.g., a receptor prevalent among the targeted cells (e.g., skin cells), or with other therapeutic or immunogenic compositions. Thus, liposomes filled with a desired inhibitor of the invention can be directed to the site of treatment, where the liposomes then deliver the selected inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. (1980) Ann. Rev. Biophys. Bioeng. 9: 467, U.S. Pat. Nos. 4,235,871, 4,501,728 and 4,837,028.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. Compounds and agents of the present invention and their physiologically acceptable salts and solvates can be formulated for administration by any suitable route, including via inhalation, topically, nasally, orally, parenterally, or rectally.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

2. Routes of Administration

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Suitable formulations for transdermal application include an effective amount of a compound or agent of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a DACT1 protein or a nucleic acid encoding a DACT1 protein, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds and agents of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the active ingredient, e.g., a DACT1 protein or a nucleic acid encoding a DACT1 protein, may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The inhibitors can also be formulated in rectal compositions, for example, suppositories or retention enemas, for example, containing conventional suppository bases, for example, cocoa butter or other glycerides.

Furthermore, the active ingredient can be formulated as a depot preparation. Such long-acting formulations can be administered by implantation (for example, subcutaneously or intramuscularly) or by intramuscular injection. Thus, for example, the active ingredient can be formulated with suitable polymeric or hydrophobic materials (for example as an emulsion in an acceptable oil) or ion exchange resins, or as sparingly soluble derivatives, for example, as a sparingly soluble salt.

A pharmaceutical composition or medicament of the present invention comprises (i) an effective amount of a compound as described herein that increases the level or activity of DACT1 protein, and (ii) another therapeutic agent. When used with a compound of the present invention, such therapeutic agent may be used individually, sequentially, or in combination with one or more other such therapeutic agents (e.g., a first therapeutic agent, a second therapeutic agent, and a compound of the present invention). Administration may be by the same or different route of administration or together in the same pharmaceutical formulation.

3. Dosage

Pharmaceutical compositions or medicaments can be administered to a subject at a therapeutically effective dose to prevent, treat, or control gastric cancer as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular compound in a particular subject. For example, each type of DACT1 protein or nucleic acid encoding a DACT1 protein will likely have a unique dosage. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

To achieve the desired therapeutic effect, compounds or agents may be administered for multiple days at the therapeutically effective daily dose. Thus, therapeutically effective administration of compounds to treat a pertinent condition or disease described herein in a subject requires periodic (e.g., daily) administration that continues for a period ranging from three days to two weeks or longer. Typically, agents will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

Optimum dosages, toxicity, and therapeutic efficacy of such compounds or agents may vary depending on the relative potency of individual compounds or agents and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any agents used in the methods of the invention, the therapeutically effective dose can be estimated initially from cell culture assays. A dose can be formulated in animal models to achieve a circulating plasma concentration range that includes the $IC_{50}$ (the concentration of the agent that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of agents is from about 1 ng/kg to 100 mg/kg for a typical subject.

Exemplary dosages for DACT1 protein or a nucleic acid encoding a DACT1 protein described herein are provided. Dosage for a DACT1-encoding nucleic acid, such as an expression cassetter, can be between 0.1-0.5 mg/eye, with intravitreous administration (e.g., 5-30 mg/kg). Small organic compounds activators can be administered orally at between 5-1000 mg, or by intravenous infusion at between 10-500 mg/ml. Monoclonal antibody activators can be administered by intravenous injection or infusion at 50-500 mg/ml (over 120 minutes); 1-500 mg/kg (over 60 minutes); or 1-100 mg/kg (bolus) five times weekly. DACT1 Protein or peptide activators can be administered subcutaneously at 10-500 mg; 0.1-500 mg/kg intravenously twice daily, or about 50 mg once weekly, or 25 mg twice weekly.

Pharmaceutical compositions of the present invention can be administered alone or in combination with at least one additional therapeutic compound. Exemplary advantageous therapeutic compounds include systemic and topical anti-inflammatories, pain relievers, anti-histamines, anesthetic compounds, and the like. The additional therapeutic compound can be administered at the same time as, or even in the same composition with, main active ingredient (e.g., a DACT1 protein or a nucleic acid encoding the protein). The additional therapeutic compound can also be administered separately, in a separate composition, or a different dosage form from the main active ingredient. Some doses of the main ingredient, such as a DACT1 protein or a nucleic acid encoding a DACT1 protein, can be administered at the same time as the additional therapeutic compound, while others are administered separately, depending on the particular symptoms and characteristics of the individual.

The dosage of a pharmaceutical composition of the invention can be adjusted throughout treatment, depending on severity of symptoms, frequency of recurrence, and physiological response to the therapeutic regimen. Those of skill in the art commonly engage in such adjustments in therapeutic regimen.

VII. KITS AND DEVICES

The invention provides compositions and kits for practicing the methods described herein to assess the level of DACT1 mRNA or DACT1 protein in a subject, which can be used for various purposes such as detecting or diagnosing the presence of gastric cancer, determining the risk of developing gastric cancer, and monitoring the progression of gastric cancer in a patient.

Kits for carrying out assays for determining DACT1 mRNA level typically include at least one oligonucleotide useful for specific hybridization with at least one segment of the DACT1 coding sequence or its complementary sequence. Optionally, this oligonucleotide is labeled with a detectable moiety. In some cases, the kits may include at least two oligonucleotide primers that can be used in the amplification of at least one segment of DACT1 DNA or mRNA by PCR, particularly by RT-PCR.

Kits for carrying out assays for determining DACT1 protein level typically include at least one antibody useful for specific binding to the DACT1 protein amino acid sequence. Optionally, this antibody is labeled with a detectable moiety. The antibody can be either a monoclonal antibody or a polyclonal antibody. In some cases, the kits may include at least two different antibodies, one for specific binding to the DACT1 protein (i.e., the primary antibody) and the other for detection of the primary antibody (i.e., the secondary antibody), which is often attached to a detectable moiety.

Typically, the kits also include an appropriate standard control. The standard controls indicate the average value of DACT1 protein or DACT1 mRNA in the stomach epithelium of healthy subjects not suffering from gastric cancer. In some cases such standard control may be provided in the form of a set value. In addition, the kits of this invention may provide instruction manuals to guide users in analyzing test samples and assessing the presence, risk, or state of gastric cancer in a test subject.

In a further aspect, the present invention can also be embodied in a device or a system comprising one or more such devices, which is capable of carrying out all or some of the method steps described herein. For instance, in some cases, the device or system performs the following steps upon receiving a stomach tissue sample, e.g., a stomach mucosa sample taken from a subject being tested for detecting gastric cancer, assessing the risk of developing gastric cancer, or monitored for progression of the condition: (a) determining in sample the amount or concentration of DACT1 mRNA, DACT1 protein; (b) comparing the amount or concentration with a standard control value; and (c) providing an output indicating whether gastric cancer is present in the subject or whether the subject is at risk of developing gastric cancer, or whether there is a change, i.e., worsening or improvement, in the subject's gastric cancer condition. In other cases, the device or system of the invention performs the task of steps (b) and (c), after step (a) has been performed and the amount or concentration from (a) has been entered into the device. Preferably, the device or system is partially or fully automated.

EXAMPLES

The following examples are provided by way of illustration only and not by way of limitation. Those of skill in the art will readily recognize a variety of non-critical parameters that could be changed or modified to yield essentially the same or similar results.

Materials And Methods
Human Gastric Specimens
Tissue Samples

Paraffin-embedded tumor tissues samples were obtained from 205 gastric cancer patients diagnosed in the First Affiliated Hospital of Sun Yat-sen University, Guangzhou, China, from January 1999 to December 2006. In addition, 20 age-matched subjects with normal upper gastroscopy were recruited as control. The study protocol was approved by the Clinical Research Ethics Committee of the Sun Yat-sen University of Medical Sciences.

Tumor Cell Line

Ten gastric cancer cell lines (AGS, Kato III, MKN28, MKN45, N87, SNU1, SNU16, SNU719, BGC823 and MGC803) and one normal gastric epithelial cell line (GES1) were used in this study. Cell lines were maintained in RPMI-1640 or DMEM medium (Gibco BRL, Rockville, Md.) with 10% fetal bovine serum.

Gene Expression Analysis
RNA Isolation

Total RNA was isolated using Qiazol reagent (Qiagen, Valencia, Calif., USA). First, about $5\text{-}10\times10^6$ cells or 30 mg tissue was homogenized in 1 mL Qiazol reagent and incubated at room temperature for 10 min. For each sample, 0.2 mL chloroform was added. The mixture should be shaken vigorously for 15 sec and placed at room temperature for another 3 min. Samples were centrifuged at 12,000 g for 20 min at 4° C. and separated into two layers. The upper aqueous phase containing RNA was transferred to a new tube, mixed with 0.7 ml isopropanol, incubated at room temperature for 10 min and then centrifuged at 12,000 g for 10 min at 4° C. After discarding the supernatant, the RNA pellet was washed twice with 1 mL 75% ethanol; air dried for 5 min and re-dissolved the RNA with RNase-free $H_2O$. Contamination of DNA was eliminated by the RNase-free DNaseI digestion (GE Healthcare, Buckinghamshire, England). The quality and quantity of total RNA were determined by measuring absorbance at 260 nm/280 nm using NanoDrop ND-1000

(NanoDrop Technologies, Wilmington, Del., USA). The purified RNA was store at −80° C. until use.

cDNA Synthesis

MultiScribe Reverse Transcriptase Kit (Applied Biosystems, Foster City, Calif., USA) was used to synthesize cDNA. The reaction mixture contained 1× Reverse Transcriptase buffer, 1× dNTP, 1× random primer (supplied by kit), 2.5 U/μL reverse transcriptase, 1 U/μL RNase inhibitor and 2 μg total RNA. The mixture was incubated at 25° C. for 10 min, then 37° C. for 120 min, then 85° C. 5 min to inactivate the enzymes. The cDNA was stored at −80° C. until other application.

Semiquantitative Reverse Transcription PCR(RT-PCR)

Semiquantitative RT-PCR was performed in a total volume of 25 μL reaction containing GeneAmp 1×PCR Buffer II (Applied Biosystems), 2.5 mM $MgCl_2$, 200 μM each of dNTP, 200 nM each of primers, 0.5 U of AmpliTaq Gold DNA polymerase (Applied Biosystems) and 30~50 ng cDNA. The PCR program started with an initial denaturation at 95° C. for 10 min, followed by 32-35 cycles (94° C. for 30 sec, annealing temperature for 30 sec, and 72° C. for 30 sec) of amplification, with a final extension at 72° C. for 10 min. The PCR bands were visualized under ultraviolet light and photographed. The expression of the target gene was normalized by the expression of house keeping gene β-actin, which served as an internal control. All primers used to amplify the transcripts are listed in Table 1.

DNA Methylation Analysis

Genomic DNA Extraction

Genomic DNA from GC cell lines and tissue samples were isolated by using DNA mini kit (Qiagen) according to the kit protocol. About 25 mg samples were lysed in 180 μL of QIAamp ATL buffer and 20 μL of proteinase K in a 1.5 mL microcentrifuge tubes for 1 hour at 56° C. Four microliter of RNase A (100 mg/ml, QIAgen) was added and mixed by pulse-vortexing for 15 s followed by 2 min incubation at room temperature. Then 200 μL of AL buffer was added to the lysate and samples were incubated for 10 min at 70° C. After adding 200 μL, of absolute ethanol, the solution was mixed by pulse-vortexing for 15 s. Then lysates were purified over a QIAamp column as specified by the manufacturer. The genomic DNA was diluted in 200 μL DNase-free $H_2O$. The quality and quantity of DNA were determined by measuring absorbance at 260 nm/280 nm using NanoDrop ND-1000 (NanoDrop).

Sodium Bisulfite Conversion

The genomic DNA was modified by sodium metabisulfite as description by Tao et al., 2002, *Hum. Mol. Genet.*, 11(18): 2091-2101. Briefly, 5 μg genomic DNA in 30 μL TE buffer (Sigma-Aldrich) was mixed with 3.3 μL of 3 mM NaOH to a final concentration of 0.3 mM and incubate at 37° C. for 15 min. Denatured DNA was mixed with 333 μL of bisulfite solution and treated in darkness for 4 hr at 55° C. The bisulfite solution was prepared as 2.4 M sodium metabisulfite (pH 5.0-5.2) (Sigma-Aldrich) and 0.5 mM hydroquinone (Sigma-Aldrich). The treated DNA was desalted and purified using the Qiaex II kit (Qiagen) according to the protocol supplied by the kit. DNA was then treated with 0.3 M NaOH at 37° C. for 15 min and precipitated with 3 M ammonium acetate and 3 volumes of ethanol. Recovered DNA was dissolved in 100 μL TE buffer (pH 8.0) and stored at −20° C.

Demethylation Treatment Using 5-aza-2'-deoxycytidine ("5-Aza")

Cells were seeded at a density of 1×105/100-mm dishes and grew for 24 hr. Cells were then treated with 2 μM 5-aza-2'-deoxycytidine ("5-Aza") (Sigma-Aldrich) for 5 days. The 5-Aza was replenished every day. The gene expression of DACT1 was evaluated using semiquantitative RT-PCR.

Methylation Specific PCR (MSP)

Methylation specific and unmethylation specific primers were designed to assess methylation status in the GC cell lines. The mixture for PCR contained 1×PCR Buffer II (Applied Biosystems), 2 mM $MgCl_2$, 200 μM each of dNTP, 600 nM each of primers, 0.5 U of AmpliTaq Gold DNA polymerase (Applied Biosystems) and 20 ng bisulfite treated DNA. The PCR program was 95° C. for 10 min, followed by 38 cycles (94° C. for 30 sec, 60° C. for 30 sec, and 72° C. for 30 sec) of amplification, with a final extension at 72° C. for 5 min. Bands of MSP were observed under ultraviolet light and photographed.

Direct Bisulfite Genomic Sequencing (BGS)

Bisulfite treated DNA was amplified with primers listed in Table 1. PCR amplification with 2 μL of bisulfite-treated DNA gives a PCR product of about 170 bp, containing 9 CpG dinucleotides at the DACT1 promoter region. Amplified BGS products were sequenced. Sequencing analysis was performed by SeqScape software (Applied Biosystems, Foster City, Calif.).

Array Comparative Genomic Hybridization (Array CGH)

DNA from five gastric cancer cell lines (MKN45, MKN28, KatoIII, N87, SUN1) and normal gastric tissue reference sample were labelled differentially, using different fluorophores, and hybridized to Array-CGH (Agilent Technologies, Santa Clara, Calif.). The results were analyzed by Agilent G4175AA CGH Analytics 3.4 (Agilent Technologies). The ratio of the fluorescence intensity of the gastric cancer cell line to the normal reference DNA was then calculated to assess the copy number changes for a particular location in the genome. Two probes were employed to detect the copy number change of DACT1 gene: locus I was at chr14, from 58177255 to 58177309, locus II was located at chr14, from 58179290 to 58179349.

Biological Function Analysis

Cloning of DACT1α and Construction of Expression Vector

The full-length cDNA of DACT1α gene expression vector was generated by PCR-cloning. Total RNA from human stomach (Ambion, Austin, Tex., USA) was reverse transcribed into cDNA. Sequence corresponding to the open reading frame (ORF) of DACT1α was amplified by PCR. PCR product was cloned into the pcDNA3.1 expression vector and pBABE-puro vector.

DACT1α Gene Transfection

Cells were seeded at ~6×10⁵ cells on a 6-well plate without antibiotics for about 24 hr till the cell density reached about 90% confluent. Cells were then transfected with 2 μg DACT1α and control vector (pcDNA3.1) respectively using Lipofectamine 2000 (Invitrogen). Lipofectamine 2000 (6.0 μL) diluted in 125 μL Opti-MEM (Invitrogen) was incubate at room temperature for 5 min. Then, plasmid DNA diluted in 125 μL Opti-MEM was combined with the Lipofectamine mixture. After 24~48 hr incubation at 37° C. in a 5% $CO_2$ incubator, cells were harvested for testing of transgenic expression. For stable cell lines, cells were passaged at a 1:10 ratio into fresh growth medium with proper concentration of neomycin (G418) (Invitrogen). Stable transfection cells were harvested after 14-21 days of selection for functional assays.

Colony Formation Assay

Two days after transfection, cells were subsequently split at 1:20 ratio on six-well plates with RPMI1640 in 10% FBS containing 500 μg/mL neomycin (G418). After 14-18 days of selection, cells were fixed with 70% ethanol for 10 min and stained with 0.5% crystal violet solution for 10 min. Colony with more than 50 cells per colony was counted. The experiment was conducted in three independent triplicates.

Annexin V Apoptosis Assay

Annexin V is a protein that could bind the cell membrane after apoptosis have occurred and before membrane integrity has been lost. The proportion of apoptotic cells was evaluated using Annexin V and 7-amino-actinomycin (7-AAD) double staining Briefly, the cells washed with 1×PBS was resuspended in 100 μL ice-cold annexin-binding buffer (10 mM HEPES, 140 mM NaCl and 2.5 mM $CaCl_2$, pH 7.4) containing 5 μL Annexin V conjugated with Alexa Fluor 488 (Invitrogen) and 2 μL 7-AAD staining After incubation for 15 min at room temperature, cells were mixed with additional 400 μL of ice-cold annexin-binding buffer and analyzed using flow cytometry.

Cell Spreading Assay and F-Actin Staining

BGC823 and MGC803 cells stably transfected with pcDNA3.1-DACT1 or pcDNA3.1 were collected by trypsinization, washed twice with DMEM medium and resuspended on cover slips and culture plate. Cells were allowed to spread for 6 h in DMEM and then photographed. The cover slips with spreading cells were fixed with 3% paraformaldehyde for F-actin staining Cells on cover slips were permeabilized by Triton X-100 and then blocked. For F-actin staining, cells were stained with Rhodamine phalloidin (Invitrogen). Finally, cells were washed and mounted with Mounting Medium containing DAPI (Vector Laboratories, Burlingame, Calif.). Images were captured by fluorescent microscopy.

Cell Migration and Invasion Assays

Wound-healing assay was performed for analysis of cell migration. AGS and MGC803 stably transfected with pcDNA3.1-DACT1 or pcDNA3.1 control vector were seeded into 6-well culture plates. After 24 h, the monolayer cells were scratched manually with a plastic pipette tip and subsequently washed with PBS. Cells were photographed (phase-contrast microscope) at 0 and 24 h after incubation. The distance traveled by cells was measured between the two boundaries of an acellular area and results of DACT1 transfected groups expressed as a ratio to pcDNA3.1 transfected cells. To measure the cell invasion activity, Transwell assays were done using a BD BioCoat™ Growth Factor Reduced MATRIGEL™ Invasion Chamber (BD Biosciences).

In Vivo Tumorigenicity

For retroviruses production, 293FT cells (Invitrogen) were co-transfected with pBABE-puro-DACT1α or pBABE-puro empty vector, two packaging plasmids pUMVC (Addgene) and pCMV-VSV-G (Addgene) at the ratio of 1:0.9:0.1. At 24 hours post-transfection, cells were feeded with fresh medium. After 48 hour post-transfection, the supernatant containing retrovirus pBABE-puro-DACT1α or pBABE-puro control was harvested and stored at −80° C. To generate stable DACT1α expressing or control cell line, retrovirus pBABE-puro-DACT1α or pBABE-puro control-containing supernatant was added to BGC823 cells. After 24 hour transduction, the media containing retrovirus was removed and replaced with fresh medium containing 0.5 ug/ml antibiotic puromycin (Invitrogen) for selection. Stable DACT1 expressing or control BGC823 cells ($5×10^5$ cells in 0.2 mL PBS) was injected subcutaneously into the left or the right dorsal flank of four 4-week-old male Balb/c nude mice, separately (4/group). Tumor diameter was measured every 3 days until 3 weeks. Tumor volume (mm3) was estimated by measuring the longest and shortest diameter of the tumor and calculating as follows: volume=(shortest diameter)$_2$×(longest diameter)×0.5. Care of animals and all experimental procedures were approved by the Animal Ethics Committee of the Chinese University of Hong Kong. After 3 weeks, the mice were sacrificed, and the tumors were weighed and fixed in formalin for histological analysis.

Statistical Analysis

Data are presented as mean±standard deviation (SD). The independent Student's t test was used to compare the difference between 2 preselected groups. The difference in cell growth curve or the tumor growth rate in mice was determined by repeated-measures analysis of variance (ANOVA). Relationship between DACT1 methylation and clinicopathologic characteristics of gastric cancer patients were compared using Pearson's chi-square test. Kaplan-Meier survival curve and log-rank test were used to evaluate overall survival data corresponding to DACT1 methylation status. Data were considered statistically significant when P is less than 0.05; and very significant when P is less than 0.01.

Results

Silence or Down-Regulation of DACT1 in Gastric Cancer

DACT1 is Expressed in Most of Human Tissues

DACT1 was expressed in all normal adult tissues and fetal tissues examined as well as in normal human gastric epithelial cell line (GES1) (FIG. 1A).

DACT1 is Eptigentically Suppressed in Cancer Cell Lines

Figure 2:
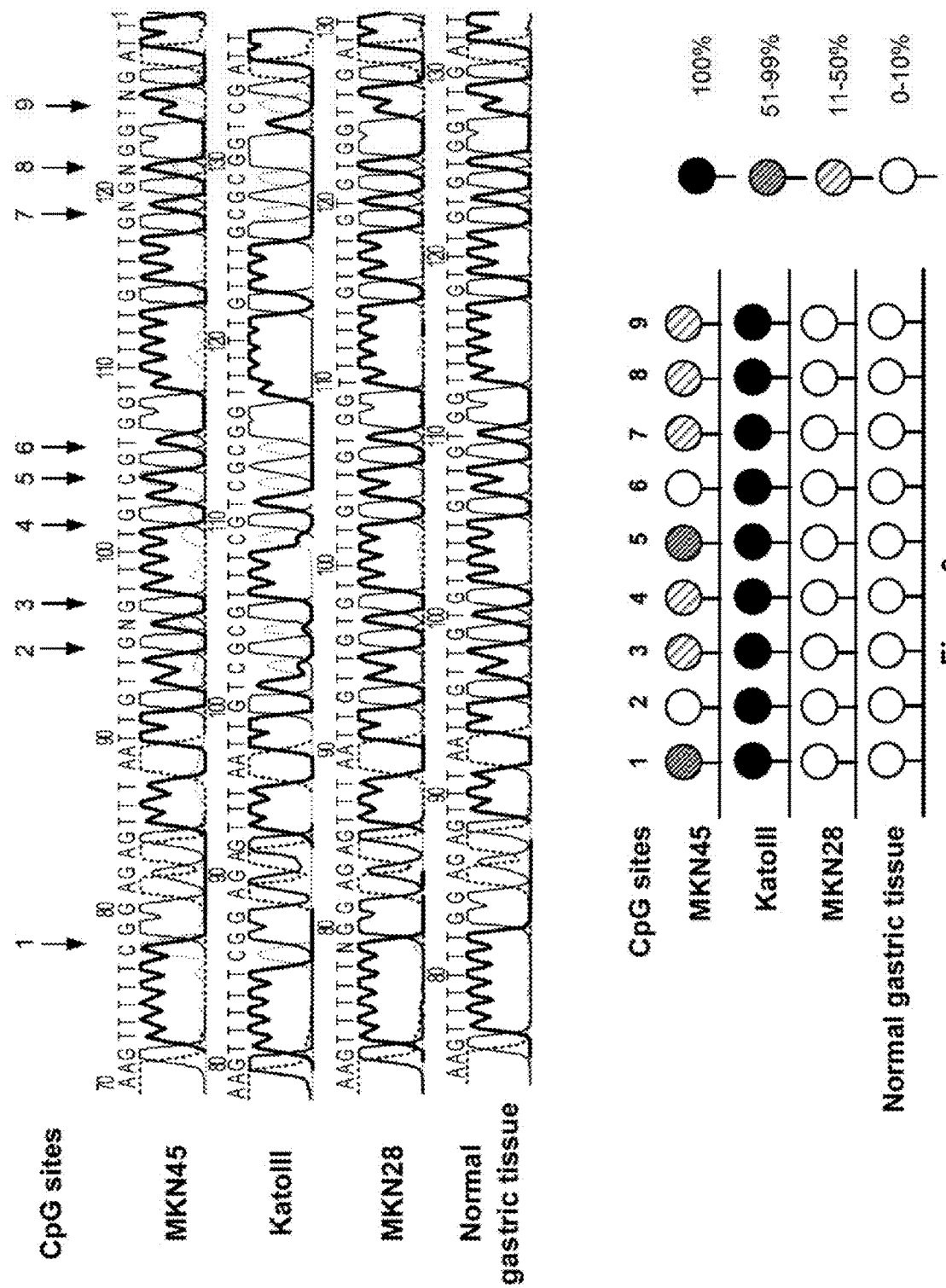
FIG. 2 shows bisulfite genomic sequencing result (SEQ ID NOS:15-18) of DACT1 promoter in gastric cancer cell lines in an embodiment.

The mRNA expression of DACT1 was silenced or reduced in 9 out of 10 gastric cancer cell lines. To elucidate the role of promoter methylation in the down-regulation of DACT1, DACT1 methylation status was examined by MSP. Methylation was observed in 5 silenced cell lines (KatoIII, AGS, MKN45, SNU719, MGC803), but not detected in normal gastric epithelial cell GES1 (FIG. 1B). The DACT1 methylation status was validated by BGS. The BGS results were consistent with those of MSP in which dense methylation was found in methylated cell lines (MKN45 and KatoIII), but not in unmethylated MKN28 and normal gastric tissues (FIG. 2).

DACT1 Expression could be Restored after Demethylation Treatment

Figure 3:
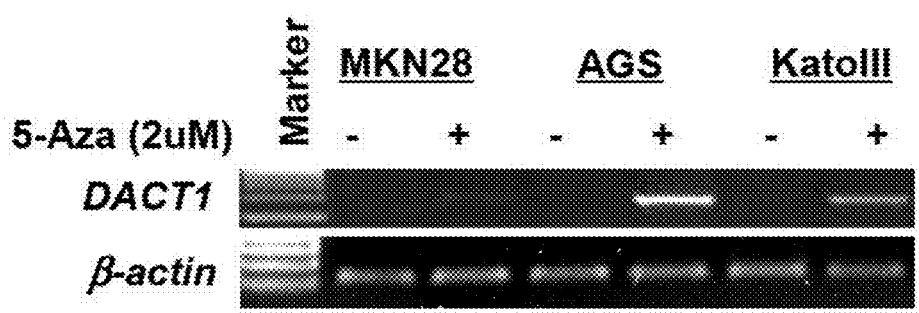
FIG. 3 shows the effect of a demethylating agent on DACT1 expression in an embodiment.

To test whether methylation directly mediates DACT1 silencing, three silenced cell lines (MKN28, AGS, KatoIII) were treated with demethylation agent 5-Aza. This treatment restored DACT1 expression in AGS and KatoIII cell lines (FIG. 3), inferring transcriptional silence of DACT1 was mediated by promoter methylation in gastric cancer cells.

Funtional Assay

Inhibition of cell proliferation by DACT1 α

Figure 4:
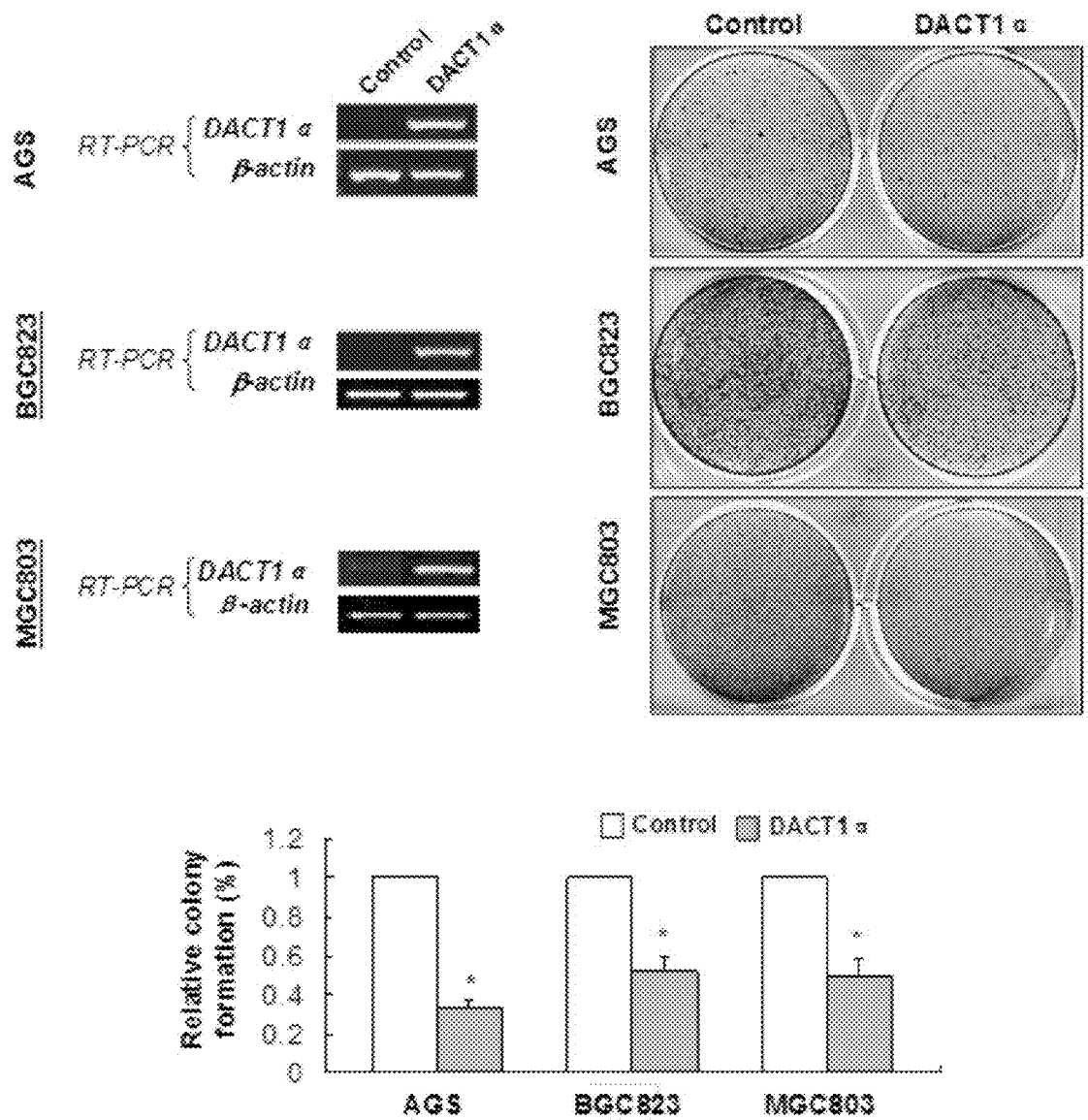
FIG. 4 shows the effect of DACT1α expression on transfected cells in colony formation assay in an embodiment.
Figure 5:
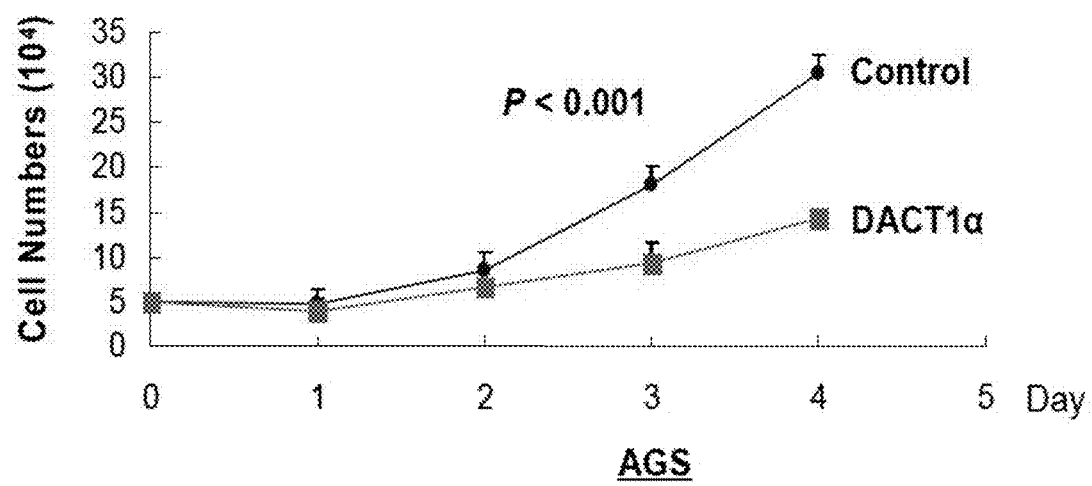
FIG. 5 shows the effect of DACT1α expression on transfected cells in cell growth curve in an embodiment.

In vitro biological effects of DACT1α on cell growth in the DACT1α non-expressing cell lines (AGS, BGC823 and MGC803) were examined by colony formation assay and cell growth curve. The colonies formed in three DACT1α-transfected cells were significantly fewer in number and smaller in size than in control vector-transfected cells (FIG. 4). Keeping with this finding, ectopic expression of DACT1α dramatically reduced cell growth curve in AGS cells (FIG. 5). Both colony formation and cell growth curve assay solidly demonstrated that DACT1α could inhibit cell growth of GC cells in vitro.

Induction of Cell Apoptosis by DACT1α

To examine the contribution of apoptosis to the observed growth inhibition of DACT1α-transfected cells, cell apoptosis was determined by flow cytometry with Annexin V-APC and 7-AAD double staining The results indicated an increase in the numbers of early apoptotic cells (BGC823: 2.73%±0.05% vs. 3.60%±0.45%, P=0.03; MGC803: 2.36%±0.25% vs. 3.63%±0.25%) in DACT1α-transfected cells than those in control vector transfected cells.

DACT1α Suppresses Gastric Cancer Cell Spreading, Migration, and Invasiveness

Figure 6:
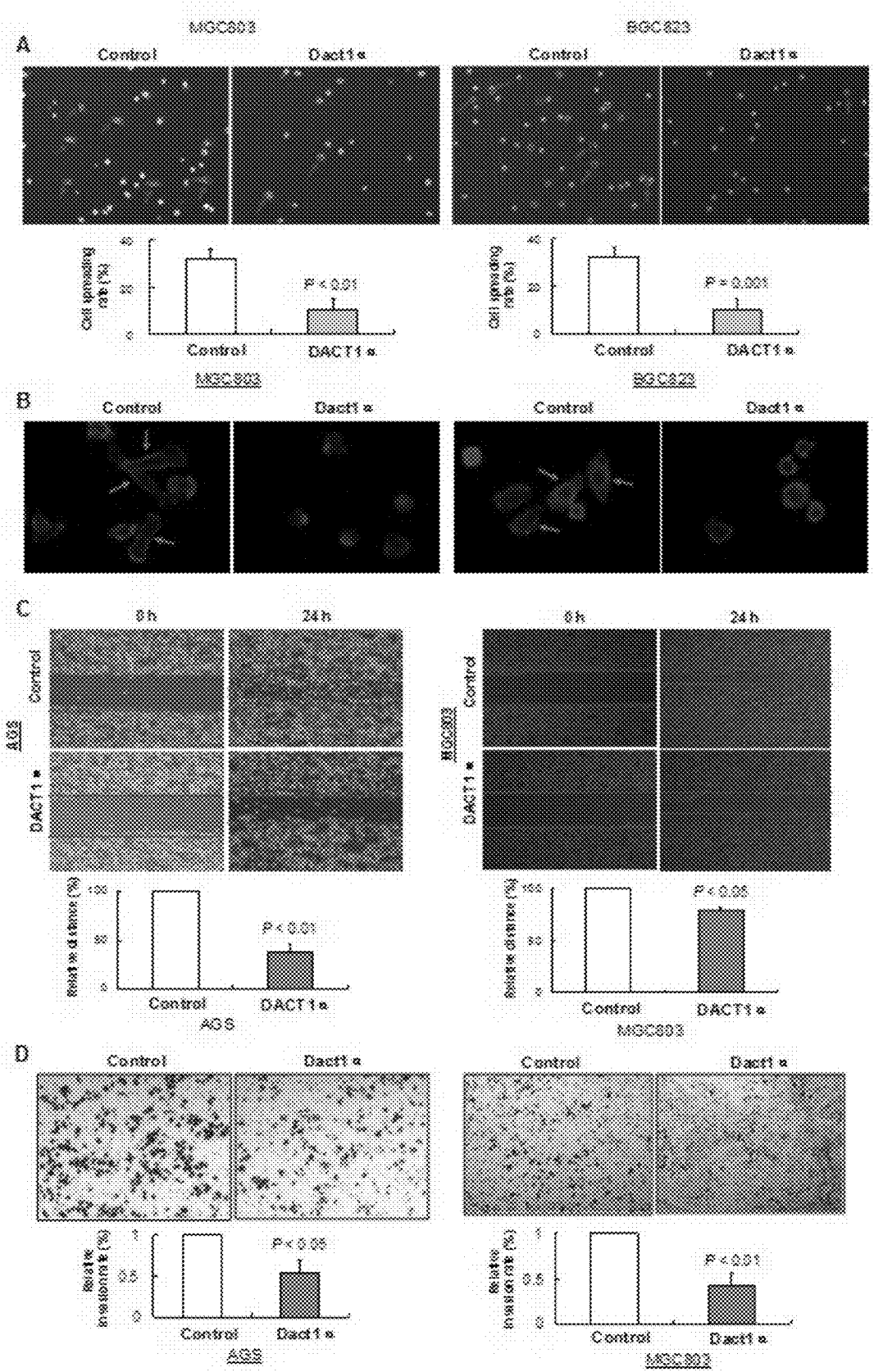
FIG. 6 shows suppressive effect of DACT1α on cell spreading, F-actin formation, cell migration and invasion ability in an embodiment.

Re-expressing of DACT1α showed a remarkable reduction in cell spreading (FIG. 6A). The extent of spreading of individual cells was substantially inhibited in DACT1α transfected BGC823 (P<0.01) and MGC803 cells (P=0.001) compared with control cells (FIG. 6A). Concomitantly, DACT1α repressed actin microfilament formation in both BGC823 and MGC803 cells by rhodamine-labeled phalloidin staining (FIG. 6B). DACT1α re-expression slowed cell migration scratchy "wound" at edges of AGS and MGC803 cells (FIG. 6C). Quantitative analyses at 24 h confirmed a significant reduction in wound closure in DACT1α transfected AGS (P<0.01) and MGC803 (P<0.05) cells compared to vector transfected control cells (FIG. 6C). In addition, DACT1α significantly dampened cell invasive ability as measured by transwell assays in AGS (P<0.05) and MGC803 (P<0.01) cells respectively (FIG. 6D).

In Vivo Tumor Suppression

Figure 7:
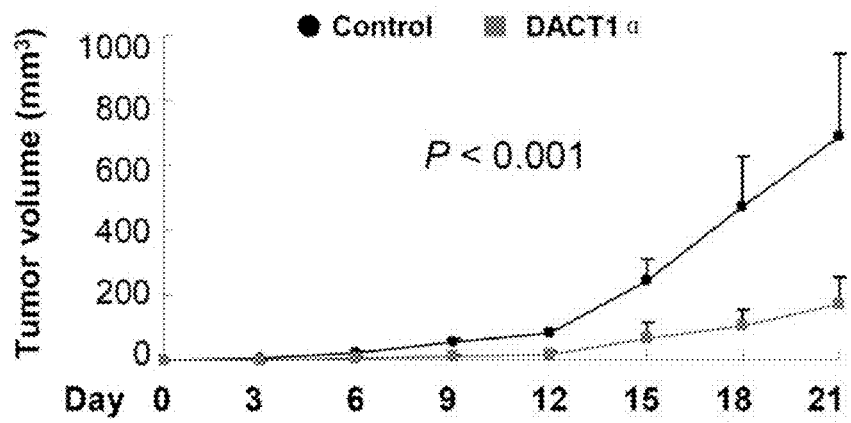
FIG. 7 shows the growth-inhibition effect of DACT1α expression in nude mice in an embodiment.
Figure 7:
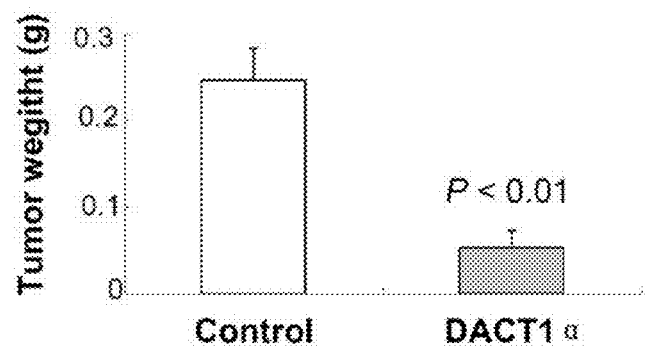

Stable DACT1α expressing and control cell lines were generated by infecting BGC823 cells with retrovirus pBABE-puro-DACT1α or pBABE-puro control and selecting with puromycin. Stable DACT1α expressing or control BGC823 cells was injected subcutaneously into the left or the right dorsal flank of 4-week-old male Balb/c nude mice to compare the tumor growth patterns in vivo. The tumor growth curve of BGC823 stably transfected with DACT1α or empty vector in vivo was shown in FIG. 7A. The tumor volume was significantly lower in DACT1α transfected nude mice as compared to the vector control mice (P<0.001). At the end of experiments, tumors were isolated and weighted. The mean tumor weight was significantly lesser in DACT1α transfected nude mice as compared with the vector control mice (P<0.01) (FIG. 7B), indicating that DACT1α acts as a tumor suppressor in gastric carcinogenesis.

Methylation Status in Gastric Cancer Patients

Methylation Status in the Gastric Cancer Tissues and Normal Gastric Tissues

Figure 8A:
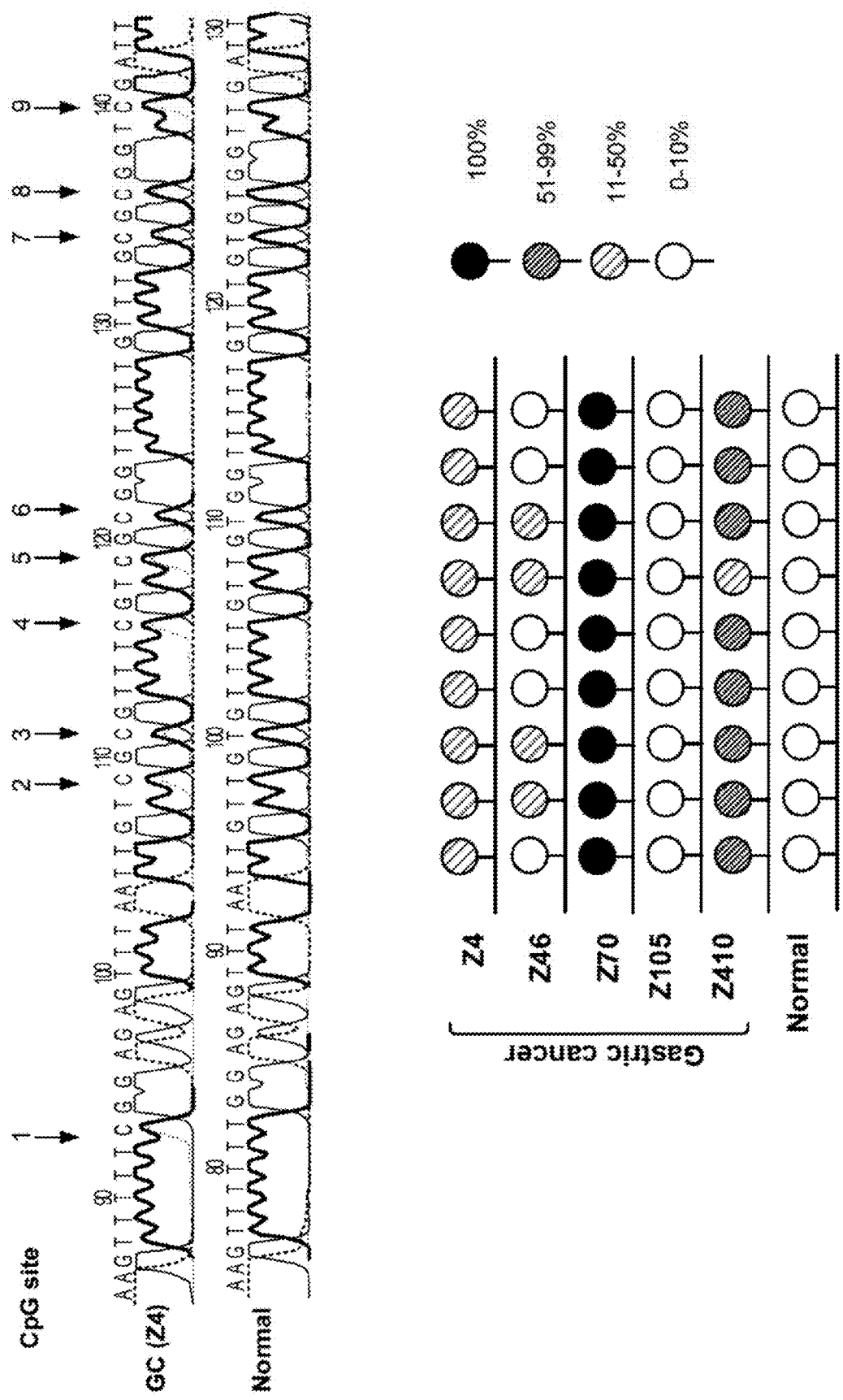
FIG. 8 shows the methylation status of DACT1 (SEQ ID NOS:16 and 18) in primary gastric cancer and normal gastric tissue samples and Kaplan-Meier analysis of gastric cancer patient survival in an embodiment.

The clinical application of DACT1 methylation was evaluated in 205 primary gastric cancers and in 20 healthy gastric tissue samples. Among 205 gastric cancer cases, partial and dense promoter methylation of DACT1 was detected in 29.3% (60/205) cases, but none in 20 healthy gastric tissue samples (FIG. 8A).

Association Between DACT1 Methylation and Clinical Characteristics

Figure 8B:
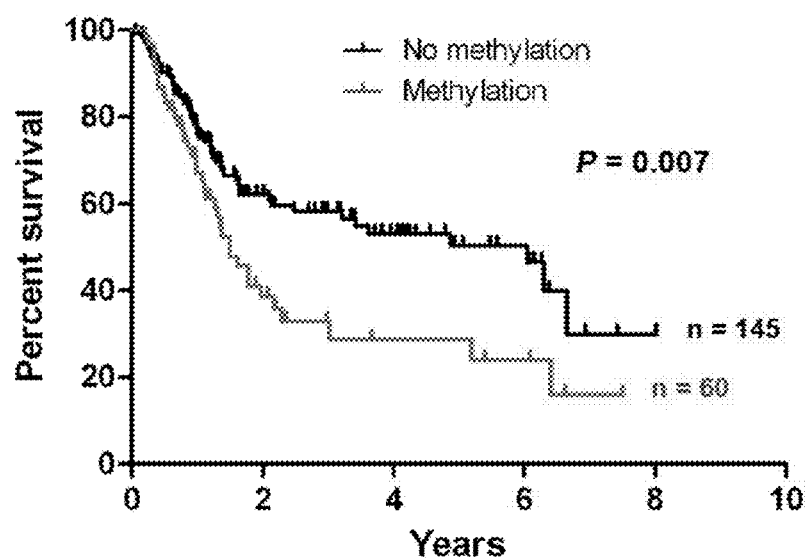

DACT1 methylation was associated with advanced tumor size (P<0.05), lymph node metastasis (P<0.05) and distant metastasis (P=0.05) (Table 2). DACT1 methylation was more frequent in TNM stage III/IV than in stage I/II cases (P<0.0005) (Table 2). Moreover, as shown in the Kaplan-Meier survival curves, gastric cancer patients with DACT1 methylation had significantly shorter survival than those without DACT1 methylation (P=0.007, log-rank test) (FIG. 8B).

All patents, patent applications, and other publications, including GenBank Accession Numbers, cited in this application are incorporated by reference in the entirety for all purposes.

TABLE 1

DNA sequences of primers used in this study

| Primer name | Sequence (5'-3') | |
|---|---|---|
| A) RT-PCR primers for detecting DACT1 mRNA expression | | |
| DACT1-F | AGGAGAAGTTCTTGGAGGAG | SEQ ID NO: 7 |
| DACT1-R | TGAGCTAGGCCGACTGTCTG | SEQ ID NO: 8 |
| B) BGS primers | | |
| DACT1-BGS-F | GTTTGGGAAGTGAAAGAAATTTAATT | SEQ ID NO: 9 |
| DACT1-BGS-R | CTAAAACCCCAACATCCTATTACAAT | SEQ ID NO: 10 |
| C) MSP primers | | |
| DACT1-MSP-MF | CGGGATAGTAGTAGTCGGC | SEQ ID NO: 11 |
| DACT1-MSP-MR | CGCTAAAACTACGACCGCG | SEQ ID NO: 12 |
| DACT1-MSP-UF | GTTGGGATAGTAGTAGTTGGT | SEQ ID NO: 13 |
| DACT1-MSP-UR | AAACACTAAAACTACAACCACA | SEQ ID NO: 14 |

TABLE 2

Clinicopathologic features of patients with gastric cancer according to the methylation status of the DACT1 promoter

| Variable | Non-methylated (n = 145) | % | Methylated (n = 60) | % | P value |
|---|---|---|---|---|---|
| Age | | | | | |
| Mean ± SD | 58 ± 11.5 | | 55 ± 13.9 | | 0.07 |
| Gender | | | | | |
| M | 102 | 70.3 | 37 | 61.7 | 0.23 |
| F | 43 | 29.7 | 23 | 38.3 | |
| *H. pylori* infection | | | | | |
| Negative | 66 | 66.7 | 20 | 64.5 | 0.83 |
| Positive | 33 | 33.3 | 11 | 35.5 | |
| Lauren | | | | | |
| Diffuse or Mixed | 25 | 17.4 | 8 | 13.6 | 0.51 |
| Intestinal | 119 | 82.6 | 51 | 86.4 | |
| Location | | | | | |
| Cardiac | 30 | 20.7 | 11 | 18.3 | 0.70 |
| Non-cardiac | 115 | 79.3 | 49 | 81.7 | |
| Differentiation | | | | | |
| Poor | 78 | 64.5 | 40 | 76.9 | 0.11 |
| Well or moderate | 43 | 35.5 | 12 | 23.1 | |
| Lymph node metastasis | | | | | |
| Negative | 37 | 31.1 | 5 | 11.9 | 0.015* |
| Positive | 82 | 68.9 | 37 | 88.1 | |
| Tumor Size | | | | | |
| I-II | 34 | 29.6 | 4 | 10.0 | 0.013* |
| III-IV | 81 | 70.4 | 36 | 90.0 | |

TABLE 2-continued

Clinicopathologic features of patients with gastric cancer according to the methylation status of the DACT1 promoter

| Variable | Non-methylated (n = 145) | % | Methylated (n = 60) | % | P value |
|---|---|---|---|---|---|
| Distant metastasis | | | | | |
| Negative | 95 | 77.9 | 27 | 62.8 | 0.05* |
| Positive | 27 | 22.1 | 16 | 37.2 | |

TABLE 2-continued

Clinicopathologic features of patients with gastric cancer according to the methylation status of the DACT1 promoter

| Variable | Non-methylated (n = 145) | % | Methylated (n = 60) | % | P value |
|---|---|---|---|---|---|
| TNM stage | | | | | |
| I-II | 51 | 38.1 | 6 | 11.3 | <0.0005* |
| III-IV | 83 | 61.9 | 47 | 88.7 | |

What is claimed is:

1. A method for detecting gastric cancer in a subject, comprising the steps of:
   (a) treating a gastric sample taken from the subject with a bisulfite;
   (b) performing a polymerase chain reaction using a primer consisting of the polynucleotide sequence of SEQ ID NO:9, 10, 11, 12, 13, or 14 and determining methylation status of each CpG in a CpG-containing genomic sequence, wherein the CpG-containing genomic sequence is the -465 to -406 -465 to -406 region from human DACT1 transcription start site or a fragment thereof that comprises at least one CpG; and
   (c) diagnosing the subject as having gastric cancer when at least one CpG in the CpG-containing genomic sequence is at least 11% methylated.

2. The method of claim 1, wherein the CpG-containing genomic sequence comprising two or more CpG, and wherein at least 50% of all CpG is at least 11% methylated.

3. The method of claim 1, wherein the CpG-containing genomic sequence is a segment of at least 15 contiguous nucleotides of the -465 to -406 region from DACT1 transcription start site.

4. The method of claim 1, wherein CpG-containing genomic sequence is a segment of at least 20 contiguous nucleotides of the -465 to -406 region from DACT1 transcription start site.

5. The method of claim 1, wherein CpG-containing genomic sequence is a segment of at least 50 contiguous nucleotides of the -465 to -406 region from DACT1 transcription start site.

6. The method of claim 1, wherein CpG-containing genomic sequence is the -465 to -406 region from DACT1 transcription start site.

7. The method of claim 1, wherein CpG-containing genomic sequence is the -465 to -406 region from DACT1 transcription start site, and wherein at least 5 of all CpG is at least 11% methylated.

8. The method of claim 1, wherein the sample is a stomach mucosa sample.

9. The method of claim 1, further comprising repeating steps (a) and (b) at a later time using the same type of sample from the subject, wherein an increase in the number of methylated CpG at the later time as compared to the number of methylated CpG determined from the original step (b) indicates a worsening of gastric cancer, and a decrease indicates an improvement of gastric cancer.

10. The method of claim 1, wherein step (b) comprises sequencing of a DNA molecule.

* * * * *

SEQUENCE LISTING

<160> NUMBER OF SEQ ID NOS: 18

<210> SEQ ID NO 1
<211> LENGTH: 184
<212> TYPE: DNA
<213> ORGANISM: Homo sapiens
<220> FEATURE:
<221> NAME/KEY: promoter
<222> LOCATION: (1)...(184)
<223> OTHER INFORMATION: promoter region for human dapper, antagonist of
      beta-catenin, homolog 1 (Xenopus laevis) (DACT1),
      positions -566 to -383 from transcription start
      site, DACT1 genomic sequence

<400> SEQUENCE: 1

```
gtttgggaag tgaaagaaat ttaattcggt gtgagtggaa atgaggagtg gtcgtgtggg      60
gaaagggtta agattgtgtt gtaatttggt cgagttttag aaagtttttc ggagagttta     120
attgtcgcgt ttcgtcgcgg tttttgtttg cgcggtcgat tgtaatagga tgttgggtt     180 ttag                                                                  184
```

<210> SEQ ID NO 2
<211> LENGTH: 2511
<212> TYPE: DNA
<213> ORGANISM: Homo sapiens
<220> FEATURE:
<221> NAME/KEY: CDS
<222> LOCATION: (1)...(2511)
<223> OTHER INFORMATION: DACT1alpha protein cDNA coding region

<400> SEQUENCE: 2

```
atgaagccga gtccggccgg gacggcgaag gagctggagc ctccggcgcc ggcccgaggc      60
gagcagcgca cggcggagcc cgaggggcgc tggcgggaga agggcgaggc agacaccgag     120
cggcagcgca cccgggagcg gcaggaggcc acgctggccg ggctggcgga gctggagtac     180
ctgcgccagc gccaagagct gctggtcagg ggcgccctgc gcggcgccgg gggtgcggga     240
gccgctgcgc cccgcgctgg ggagctactg ggggaggcgg cgcagcgcag tcgcctggag     300
gagaagttct tggaggagaa catcttgctg ctaagaaagc aattgaactg tttgaggcga     360 agatgctg gtttgttgaa tcagttgcaa gagcttgaca agcagataag tgacctgaga     420
ctggatgtag aaaagacatc tgaagagcac ctggagacag acagtcggcc tagctcaggg     480
ttttatgagc tgagtgatgg ggcttcagga tcccttttcca attcctctaa ctcggtgttc     540
agtgagtgtt tatccagttg tcattccagc acctgctttt gcagcccctt ggaggcgacc     600
ttgagtctct cagatggttg ccccaaatcg gcagatctca taggattgtt ggaatataaa     660
gaaggccact gtgaagacca ggcctcaggg gcagtttgcc gttccctctc cacaccacaa     720
tttaattccc ttgatgtcat tgcagatgtg aatcccaagt accagtgtga tctggtgtct     780
```

```
aaaaacggga atgatgtata tcgctatccc agtccacttc atgctgtggc tgtgcagagc    840
ccaatgtttc tcctttgtct gacgggcaac cctctgaggg aagaggacag gcttggaaac    900
catgccagtg acatttgcgg tggatctgag ctagatgccg tcaaaacaga cagttcctta    960
ccgtccccaa gcagtctgtg gtctgcttcc catccttcat ccagcaagaa aatggatggc   1020
tacattctga gcctggtcca gaaaaaaaca caccctgtaa ggaccaacaa accaagaacc   1080
agcgtgaacg ctgaccccac gaaagggctt ctgaggaacg ggagcgtttg tgtcagagcc   1140
ccgggcggtg tctcacaggg caacagtgtg aaccttaaga attcgaaaca ggcgtgtctg   1200
ccctctggcg ggataccttc tctgaacaat gggacattct ccccaccgaa gcagtggtcg   1260
aaagaatcaa aggccgaaca agccgaaagc aagagggtgc ccctgccaga gggctgcccc   1320
tcaggcgctg cctccgacct tcagagtaag cacctgccaa aaacggccaa gccagcctcg   1380
caagaacatg ctcggtgttc cgccattggg acaggggagt cccctaagga aagcgctcag   1440
ctctcagggg cctctccaaa agagagtcct agcagaggcc ctgccccgcc gcaggagaac   1500
aaagttgtac agcccctgaa aaagatgtca cagaaaaaca gcctgcaggg cgtccccccg   1560
gccactcctc ccctgctgtc tacagctttc cccgtggaag agaggcctgc cttggatttc   1620
aagagcgagg gctcttccca aagcctggag gaagcgcacc tggtcaaggc ccagtttatc   1680
ccggggcagc agcccagtgt caggctccac cggggccaca ggaacatggg cgtcgtgaag   1740
aactccagcc tgaagcaccg cggcccagcc ctccaggggc tggagaacgg cttgcccacc   1800
gtcagggaga aaacgcgggc cgggagcaag aagtgtcgct tcccagatga cttggataca   1860
aataagaaac tcaagaaagc ctcctccaag gggaggaaga gtggggggcgg gcccgaggct   1920 ggtgttcccg gcaggcccgc gggcgggggc cacagggcgg ggagcagggc gcatggccac   1980
ggacgggagg cggtggtggc caaacctaag cacaagcgaa ctgactaccg gcggtggaag   2040
tcctcggccg agatttccta cgaagaggcc ctgaggaggg cccggcgcgg tcgccgggag   2100
aatgtggggc tgtaccccgc gcctgtgcct ctgccctacg ccagcccta cgcctacgtg   2160 gctagcgact ccgagtactc ggccgagtgc gagtccctgt tccactccac cgtggtggac   2220
accagtgagg acgagcagag caattacacc accaactgct tcggggacag cgagtcgagt   2280
gtgagcgagg gcgagttcgt gggggagagc acaaccacca gcgactctga agaaagcggg   2340
ggcttaattt ggtcccagtt tgtccagact ctgcccattc aaacggtaac ggccccagac   2400
cttcacaacc accccgcaaa aacctttgtc aaaattaagg cctcacataa cctcaagaag   2460
aagatcctcc gctttcggtc tggctctttg aaactgatga cgacggtttg a            2511
```

<210> SEQ ID NO 3
<211> LENGTH: 3877
<212> TYPE: DNA
<213> ORGANISM: Homo sapiens
<220> FEATURE:
<223> OTHER INFORMATION: human dapper, antagonist of beta-catenin, homolog 1 (Xenopus laevis), transcript variant 1 (DACT1, DACT1alpha, DAPPER, DAPPER1, DPR1), hepatocellular carcinoma novel gene 3, dapper homolog 1, FRODO, HDPR1, THYEX3 cDNA
<220> FEATURE:
<221> NAME/KEY: CDS
<222> LOCATION: (165)...(2675)
<223> OTHER INFORMATION: DACT1alpha

<400> SEQUENCE: 3

```
ggcggtcgcg cgcaggactc gagggcttct agccaccgtc ccgcagcg ccgcgccccg     60 ccacagggcg gcatgagccc acccgcggcc gcagccctag cgccctgctc ctccgcctgg    120
```

-continued

| | |
|---|---|
| gcggcccggc tgcggtgacg gctctcgctg cccgactggg ggccatgaag ccgagtccgg | 180 |
| ccgggacggc gaaggagctg gagcctccgg cgccggcccg aggcgagcag cgcacggcgg | 240 |
| agcccgaggg gcgctggcgg gagaagggcg aggcagacac cgagcggcag cgcacccggg | 300 |
| agcggcagga ggccacgctg gccgggctgg cggagctgga gtacctgcgc cagcgccaag | 360 |
| agctgctggt caggggcgcc ctgcgcggcg ccgggggtgc gggagccgct cgccccgcg | 420 |
| ctggggagct actgggggag gcggcgcagc gcagtcgcct ggaggagaag ttcttggagg | 480 |
| agaacatctt gctgctaaga aagcaattga actgtttgag gcgaagagat gctggtttgt | 540 |
| tgaatcagtt gcaagagctt gacaagcaga taagtgacct gagactggat gtagaaaaga | 600 |
| catctgaaga gcacctggag acagacagtc ggcctagctc agggttttat gagctgagtg | 660 |
| atggggcttc aggatccctt tccaattcct ctaactcggt gttcagtgag tgtttatcca | 720 |
| gttgtcattc cagcacctgc ttttgcagcc ccttggaggc gaccttgagt ctctcagatg | 780 |
| gttgccccaa atctgcagat tcataggat tgttggaata taaagaaggc cactgtgaag | 840 |
| accaggcctc agggggcagtt tgccgttccc tctccacacc acaatttaat tcccttgatg | 900 |
| tcattgcaga tgtgaatccc aagtaccagt gtgatctggt gtctaaaaac gggaatgatg | 960 |
| tatatcgcta tcccagtcca cttcatgctg tggctgtgca gagcccaatg tttctccttt | 1020 |
| gtctgacggg caaccctctg agggaagagg acaggcttgg aaaccatgcc agtgacattt | 1080 |
| gcggtggatc tgagctagat gccgtcaaaa cagacagttc cttaccgtcc ccaagcagtc | 1140 |
| tgtggtctgc ttcccatcct tcatccagca agaaaatgga tggctacatt ctgagcctgg | 1200 |
| tccagaaaaa aacacaccct gtaaggacca acaaaccaag aaccagcgtg aacgctgacc | 1260 |
| ccacgaaagg gcttctgagg aacgggagcg tttgtgtcag agccccgggc ggtgtctcac | 1320 |
| agggcaacag tgtgaacctt aagaattcga acaggcgtg tctgccctct ggcgggatac | 1380 |
| cttctctgaa caatgggaca ttctccccac cgaagcagtg gtcgaaagaa tcaaaggccg | 1440 |
| aacaagccga aagcaagagg gtgcccctgc cagagggctg cccctcaggc gctgcctccg | 1500 |
| accttcagag taagcacctg ccaaaaacgg ccaagccagc ctcgcaagaa catgctcggt | 1560 |
| gttccgccat tgggacaggg gagtcccta aggaaagcgc tcagctctca ggggcctctc | 1620 |
| caaaagagag tcctagcaga ggccctgccc cgccgcagga gaacaaagtt gtacagcccc | 1680 |
| tgaaaaagat gtcacagaaa aacagcctgc agggcgtccc ccggccact cctcccctgc | 1740 |
| tgtctacagc tttccccgtg aagagaggc ctgccttgga tttcaagagc gagggctctt | 1800 |
| cccaaagcct ggaggaagcg cacctggtca aggcccagtt tatcccgggg cagcagccca | 1860 |
| gtgtcaggct ccaccggggc cacaggaaca tgggcgtcgt gaagaactcc agcctgaagc | 1920 |
| accgcggccc agccctccag gggctggaga cggcttgcc caccgtcagg agaaaaacgc | 1980 |
| gggccgggag caagaagtgt cgcttcccag atgacttgga tacaaataag aaactcaaga | 2040 |
| aagcctcctc caaggggagg aagagtgggg cggcccga ggctggtgtt ccggcaggc | 2100 |
| ccgcgggcgg gggccacagg gcggggagca gggcgcatgg ccacggacgg gagcggtgg | 2160 |
| tggccaaacc taagcacaag cgaactgact accggcggtg gaagtcctcg gccgagattt | 2220 |
| cctacgaaga ggccctgagg agggcccggc gcggtcgccg ggagaatgtg gggctgtacc | 2280 |
| ccgcgcctgt gcctctgccc tacgccagcc cctacgccta cgtggctagc gactccgagt | 2340 |
| actcggccga gtgcgagtcc ctgttccact ccaccgtggt ggacaccagt gaggacgagc | 2400 |
| agagcaatta caccaccaac tgcttcgggg acagcgagtc gagtgtgagc gagggcgagt | 2460 |

```
tcgtggggga gagcacaacc accagcgact ctgaagaaag cgggggctta atttggtccc    2520
agtttgtcca gactctgccc attcaaacgg taacggcccc agaccttcac aaccacccg     2580 caaaaacctt tgtcaaaatt aaggcctcac ataacctcaa gaagaagatc ctccgctttc    2640
ggtctggctc tttgaaactg atgacgacgg tttgagtgac atcattggtg tagaaagttt    2700
gtgtgttttt ttttcttctc cctagttgcc aaaattaaaa aggtggtgtt ttcattttg     2760 tataatactt taatggaatg cttttaaaa aatataaaa ccaaggtaaa ttattgtttc      2820
atcttcacgt atggatgcta gtgcctttaa tggaaggtaa agaatgtttt gctagttaga    2880
agtacatatt gaggttttaa tggtggtgat agtgagtttt gtggcaccag ctgttttta     2940 ttttaaactt tctgagcatc cggcaaggta caggttttga tgttcaagtt ttattgggat    3000 aagatcttt gatcccaagg tcaggtggat ggaattttg gattatatt tgttccttga      3060 gtcttcaggg cagtgtctcc atgagggttt tcctgttgag gggcaccaca tacaatagtg    3120
tgaagtaggt atgaggggca gtcattgtat tctatagttt ttttatgtag tctacatttc    3180
tcagatgtat ccccattcgg ttttattctc agaactgtta ctagactcat gacttggagg    3240 ccaaaccta aatccagaga tagcagcctc gatagggacc ttaaaaggat tcacaaaaac    3300
ttttgccaca cttggtgcct aggccctgtt cctaataacc cctctagg   ccgtttatcc   3360 aacatttaga tgccttcttt tccctcccta atttgtagcc agtccaacct ttcattcctt    3420
ggaggattta gtttggat aaaattttgg tccttgggca cagagacatt cactattaat     3480
gaagtaaccc ttgggcatga ctccaatccc agaattgctc actgagcgct atgccaccga    3540
agcgttgacc tgaacatatt agtgcaatcc agtccagatt ggaccttga tcctatgtgg    3600 aagggctgtt ttttaagaaa aattttgg taaacagtat tgtgtaaaat tgcttttgt      3660 ataccaatat atgcatgttt tgtgcatgag tagtacttgt gttgatactc ctgttgatgt    3720
taaattacta tataatataa acagtatgtg ttttttatata tcattgtgta aatttaatat   3780
aacatatgca gtaataaacc atttgtttta ctgctgttaa gtttgttatt tgggtataaa    3840
accagatgtt tacacctgta aaaaaaaaaa aaaaaaa                             3877
```

<210> SEQ ID NO 4
<211> LENGTH: 179
<212> TYPE: DNA
<213> ORGANISM: Homo sapiens
<220> FEATURE:
<223> OTHER INFORMATION: partial coding sequence used to detect human
    DACT1 mRNA

<400> SEQUENCE: 4

```
aggagaagtt cttggaggag aacatcttgc tgctaagaaa gcaattgaac tgtttgaggc     60
gaagagatgc tggtttgttg aatcagttgc aagagcttga caagcagata agtgacctga   120
gactggatgt agaaaagaca tctgaagagc acctggagac agacagtcgg cctagctca    179
```

<210> SEQ ID NO 5
<211> LENGTH: 836
<212> TYPE: PRT
<213> ORGANISM: Homo sapiens
<220> FEATURE:
<223> OTHER INFORMATION: human dapper, antagonist of beta-catenin,
    homolog 1 (Xenopus laevis), isoform 1 (DACT1, DACT1alpha, DAPPER,
    DAPPER1, DPR1), hepatocellular carcinoma novel gene 3, dapper
    homolog 1, FRODO, HDPR1, THYEX3

<400> SEQUENCE: 5

Met Lys Pro Ser Pro Ala Gly Thr Ala Lys Glu Leu Glu Pro Pro Ala

-continued

```
  1               5               10              15
Pro Ala Arg Gly Glu Gln Arg Thr Ala Glu Pro Glu Gly Arg Trp Arg
                20              25              30
Glu Lys Gly Glu Ala Asp Thr Glu Arg Gln Arg Thr Arg Glu Arg Gln
                35              40              45
Glu Ala Thr Leu Ala Gly Leu Ala Glu Leu Glu Tyr Leu Arg Gln Arg
                50              55              60
Gln Glu Leu Leu Val Arg Gly Ala Leu Arg Gly Ala Gly Gly Ala Gly
65              70              75              80
Ala Ala Ala Pro Arg Ala Gly Glu Leu Leu Gly Glu Ala Ala Gln Arg
                85              90              95
Ser Arg Leu Glu Glu Lys Phe Leu Glu Glu Asn Ile Leu Leu Leu Arg
                100             105             110
Lys Gln Leu Asn Cys Leu Arg Arg Arg Asp Ala Gly Leu Leu Asn Gln
                115             120             125
Leu Gln Glu Leu Asp Lys Gln Ile Ser Asp Leu Arg Leu Asp Val Glu
                130             135             140
Lys Thr Ser Glu Glu His Leu Glu Thr Asp Ser Arg Pro Ser Ser Gly
145             150             155             160
Phe Tyr Glu Leu Ser Asp Gly Ala Ser Gly Ser Leu Ser Asn Ser Ser
                165             170             175
Asn Ser Val Phe Ser Glu Cys Leu Ser Ser Cys His Ser Ser Thr Cys
                180             185             190
Phe Cys Ser Pro Leu Glu Ala Thr Leu Ser Leu Ser Asp Gly Cys Pro
                195             200             205
Lys Ser Ala Asp Leu Ile Gly Leu Leu Glu Tyr Lys Glu Gly His Cys
                210             215             220
Glu Asp Gln Ala Ser Gly Ala Val Cys Arg Ser Leu Ser Thr Pro Gln
225             230             235             240
Phe Asn Ser Leu Asp Val Ile Ala Asp Val Asn Pro Lys Tyr Gln Cys
                245             250             255
Asp Leu Val Ser Lys Asn Gly Asn Asp Val Tyr Arg Tyr Pro Ser Pro
                260             265             270
Leu His Ala Val Ala Val Gln Ser Pro Met Phe Leu Leu Cys Leu Thr
                275             280             285
Gly Asn Pro Leu Arg Glu Glu Asp Arg Leu Gly Asn His Ala Ser Asp
                290             295             300
Ile Cys Gly Gly Ser Glu Leu Asp Ala Val Lys Thr Asp Ser Ser Leu
305             310             315             320
Pro Ser Pro Ser Ser Leu Trp Ser Ala Ser His Pro Ser Ser Ser Lys
                325             330             335
Lys Met Asp Gly Tyr Ile Leu Ser Leu Val Gln Lys Lys Thr His Pro
                340             345             350
Val Arg Thr Asn Lys Pro Arg Thr Ser Val Asn Ala Asp Pro Thr Lys
                355             360             365
Gly Leu Leu Arg Asn Gly Ser Val Cys Val Arg Ala Pro Gly Gly Val
                370             375             380
Ser Gln Gly Asn Ser Val Asn Leu Lys Asn Ser Lys Gln Ala Cys Leu
385             390             395             400
Pro Ser Gly Gly Ile Pro Ser Leu Asn Asn Gly Thr Phe Ser Pro Pro
                405             410             415
Lys Gln Trp Ser Lys Glu Ser Lys Ala Glu Gln Ala Glu Ser Lys Arg
                420             425             430
```

```
Val Pro Leu Pro Glu Gly Cys Pro Gly Ala Ala Ser Asp Leu Gln
        435                 440                 445

Ser Lys His Leu Pro Lys Thr Ala Lys Pro Ala Ser Gln Glu His Ala
    450                 455                 460

Arg Cys Ser Ala Ile Gly Thr Gly Glu Ser Pro Lys Glu Ser Ala Gln
465                 470                 475                 480

Leu Ser Gly Ala Ser Pro Lys Glu Ser Pro Ser Arg Gly Pro Ala Pro
                485                 490                 495

Pro Gln Glu Asn Lys Val Val Gln Pro Leu Lys Lys Met Ser Gln Lys
            500                 505                 510

Asn Ser Leu Gln Gly Val Pro Pro Ala Thr Pro Pro Leu Leu Ser Thr
            515                 520                 525

Ala Phe Pro Val Glu Glu Arg Pro Ala Leu Asp Phe Lys Ser Glu Gly
        530                 535                 540

Ser Ser Gln Ser Leu Glu Ala His Leu Val Lys Ala Gln Phe Ile
545                 550                 555                 560

Pro Gly Gln Gln Pro Ser Val Arg Leu His Arg Gly His Arg Asn Met
                565                 570                 575

Gly Val Val Lys Asn Ser Ser Leu Lys His Arg Gly Pro Ala Leu Gln
            580                 585                 590

Gly Leu Glu Asn Gly Leu Pro Thr Val Arg Glu Lys Thr Arg Ala Gly
        595                 600                 605

Ser Lys Lys Cys Arg Phe Pro Asp Asp Leu Asp Thr Asn Lys Lys Leu
610                 615                 620

Lys Lys Ala Ser Ser Lys Gly Arg Lys Ser Gly Gly Pro Glu Ala
625                 630                 635                 640

Gly Val Pro Gly Arg Pro Ala Gly Gly His Arg Ala Gly Ser Arg
                645                 650                 655

Ala His Gly His Gly Arg Glu Ala Val Val Ala Lys Pro Lys His Lys
            660                 665                 670

Arg Thr Asp Tyr Arg Arg Trp Lys Ser Ser Ala Glu Ile Ser Tyr Glu
        675                 680                 685

Glu Ala Leu Arg Arg Ala Arg Arg Gly Arg Arg Glu Asn Val Gly Leu
    690                 695                 700

Tyr Pro Ala Pro Val Pro Leu Pro Tyr Ala Ser Pro Tyr Ala Tyr Val
705                 710                 715                 720

Ala Ser Asp Ser Glu Tyr Ser Ala Glu Cys Glu Ser Leu Phe His Ser
                725                 730                 735

Thr Val Val Asp Thr Ser Glu Asp Glu Gln Ser Asn Tyr Thr Thr Asn
            740                 745                 750

Cys Phe Gly Asp Ser Glu Ser Val Ser Gly Glu Phe Val Gly
        755                 760                 765

Glu Ser Thr Thr Thr Ser Asp Ser Glu Glu Ser Gly Gly Leu Ile Trp
    770                 775                 780

Ser Gln Phe Val Gln Thr Leu Pro Ile Gln Thr Val Thr Ala Pro Asp
785                 790                 795                 800

Leu His Asn His Pro Ala Lys Thr Phe Val Lys Ile Lys Ala Ser His
                805                 810                 815

Asn Leu Lys Lys Lys Ile Leu Arg Phe Arg Ser Gly Ser Leu Lys Leu
            820                 825                 830

Met Thr Thr Val
        835
```

<210> SEQ ID NO 6
<211> LENGTH: 120
<212> TYPE: DNA
<213> ORGANISM: Homo sapiens
<220> FEATURE:
<221> NAME/KEY: promoter
<222> LOCATION: (0)...(120)
<223> OTHER INFORMATION: promoter region for human dapper, antagonist of
      beta-catenin, homolog 1 (Xenopus laevis) (DACT1),
      positions -18 to +102 from transcription start
      site, DACT1 genomic sequence

<400> SEQUENCE: 6
gccgggacag cagcagccgg cggtcgcgcg caggactcga gggcttctag ccaccgtccc      60
cgccagcgcc gcgccccgcc acagggcggc atgagcccac ccgcggccgc agccctagcg     120

<210> SEQ ID NO 7
<211> LENGTH: 20
<212> TYPE: DNA
<213> ORGANISM: Artificial Sequence
<220> FEATURE:
<223> OTHER INFORMATION: synthetic RT-PCR primer DACT1-F for detecting
      DACT1 mRNA expression

<400> SEQUENCE: 7
aggagaagtt cttggaggag                                                  20

<210> SEQ ID NO 8
<211> LENGTH: 20
<212> TYPE: DNA
<213> ORGANISM: Artificial Sequence
<220> FEATURE:
<223> OTHER INFORMATION: synthetic RT-PCR primer DACT1-R for detecting
      DACT1 mRNA expression

<400> SEQUENCE: 8
tgagctaggc cgactgtctg                                                  20

<210> SEQ ID NO 9
<211> LENGTH: 26
<212> TYPE: DNA
<213> ORGANISM: Artificial Sequence
<220> FEATURE:
<223> OTHER INFORMATION: synthetic direct bisulfite genomic sequencing
      (BGS) primer DACT1-BGS-F

<400> SEQUENCE: 9
gtttgggaag tgaaagaaat ttaatt                                           26

<210> SEQ ID NO 10
<211> LENGTH: 26
<212> TYPE: DNA
<213> ORGANISM: Artificial Sequence
<220> FEATURE:
<223> OTHER INFORMATION: synthetic direct bisulfite genomic sequencing
      (BGS) primer DACT1-BGS-R

<400> SEQUENCE: 10
ctaaaacccc aacatcctat tacaat                                           26

<210> SEQ ID NO 11
<211> LENGTH: 19
<212> TYPE: DNA
<213> ORGANISM: Artificial Sequence
<220> FEATURE:
<223> OTHER INFORMATION: synthetic methylation specific PCR (MSP) primer
      DACT1-MSP-MF

<400> SEQUENCE: 11
cgggatagta gtagtcggc					19

<210> SEQ ID NO 12
<211> LENGTH: 19
<212> TYPE: DNA
<213> ORGANISM: Artificial Sequence
<220> FEATURE:
<223> OTHER INFORMATION: synthetic methylation specific PCR (MSP) primer
      DACT1-MSP-MR

<400> SEQUENCE: 12
cgctaaaact acgaccgcg					19

<210> SEQ ID NO 13
<211> LENGTH: 21
<212> TYPE: DNA
<213> ORGANISM: Artificial Sequence
<220> FEATURE:
<223> OTHER INFORMATION: synthetic methylation specific PCR (MSP) primer
      DACT1-MSP-UF

<400> SEQUENCE: 13
gttgggatag tagtagttgg t					21

<210> SEQ ID NO 14
<211> LENGTH: 22
<212> TYPE: DNA
<213> ORGANISM: Artificial Sequence
<220> FEATURE:
<223> OTHER INFORMATION: synthetic methylation specific PCR (MSP) primer
      DACT1-MSP-UR

<400> SEQUENCE: 14
aaacactaaa actacaacca ca				22

<210> SEQ ID NO 15
<211> LENGTH: 60
<212> TYPE: DNA
<213> ORGANISM: Artificial Sequence
<220> FEATURE:
<223> OTHER INFORMATION: synthetic direct bisulfite genomic sequencing
      (BGS) of DACT1 promoter in gastric cancer cell line MKN45
<220> FEATURE:
<221> NAME/KEY: modified_base
<222> LOCATION: (1)...(60)
<223> OTHER INFORMATION: n = g, a, c or t

<400> SEQUENCE: 15
aagtttttcg gagagtttaa ttgttgngtt ttgtcgtggt ttttgtttgn gnggtngatt		60

<210> SEQ ID NO 16
<211> LENGTH: 60
<212> TYPE: DNA
<213> ORGANISM: Artificial Sequence
<220> FEATURE:
<223> OTHER INFORMATION: synthetic direct bisulfite genomic sequencing
      (BGS) of DACT1 promoter in gastric cancer cell line Kato III and
      primary gastric cancer (GC (Z4))

<400> SEQUENCE: 16
aagtttttcg gagagtttaa ttgtcgcgtt tcgtcgcggt ttttgtttgc gcggtcgatt		60

<210> SEQ ID NO 17
<211> LENGTH: 60
<212> TYPE: DNA

```
<213> ORGANISM: Artificial Sequence
<220> FEATURE:
<223> OTHER INFORMATION: synthetic direct bisulfite genomic sequencing
      (BGS) of DACT1 promoter in gastric cancer cell line MKN28
<220> FEATURE:
<221> NAME/KEY: modified_base
<222> LOCATION: (9)...(9)
<223> OTHER INFORMATION: n = g, a, c or t

<400> SEQUENCE: 17
aagtttttng gagagtttaa ttgttgtgtt ttgttgtggt ttttgtttgt gtggttgatt    60

<210> SEQ ID NO 18
<211> LENGTH: 60
<212> TYPE: DNA
<213> ORGANISM: Artificial Sequence
<220> FEATURE:
<223> OTHER INFORMATION: synthetic direct bisulfite genomic sequencing
      (BGS) of DACT1 promoter in normal gastric tissue

<400> SEQUENCE: 18
aagttttttg gagagtttaa ttgttgtgtt ttgttgtggt ttttgtttgt gtggttgatt    60
```